(12) United States Patent
Nagaoka

(10) Patent No.: US 9,982,242 B2
(45) Date of Patent: May 29, 2018

(54) PROTEIN COMPLEX CAPABLE OF CATALYZING ASYMMETRIC OXIDATION REACTION AND METHOD FOR PRODUCING SAME

(71) Applicant: SANYO FOODS CO., LTD., Minato-ku, Tokyo (JP)

(72) Inventor: Hiroyuki Nagaoka, Maebashi (JP)

(73) Assignee: SANYO FOODS CO., LTD., Tokyo (JP)

(*) Notice: Subject to any disclaimer, the term of this patent is extended or adjusted under 35 U.S.C. 154(b) by 288 days.

(21) Appl. No.: 14/441,657

(22) PCT Filed: Nov. 8, 2013

(86) PCT No.: PCT/JP2013/080351
§ 371 (c)(1),
(2) Date: May 8, 2015

(87) PCT Pub. No.: WO2014/073673
PCT Pub. Date: May 15, 2014

(65) Prior Publication Data
US 2015/0284693 A1 Oct. 8, 2015

(30) Foreign Application Priority Data
Nov. 9, 2012 (JP) .................... 2012-247945

(51) Int. Cl.
| A61K 8/64 | (2006.01) |
| A61L 27/04 | (2006.01) |
| C12N 9/04 | (2006.01) |
| C12P 41/00 | (2006.01) |
| C12P 7/22 | (2006.01) |
| C12N 9/02 | (2006.01) |
| C12N 9/08 | (2006.01) |

(52) U.S. Cl.
CPC ......... *C12N 9/0006* (2013.01); *C12N 9/0053* (2013.01); *C12N 9/0065* (2013.01); *C12P 7/22* (2013.01); *C12P 41/002* (2013.01); *C12Y 101/05* (2013.01); *C12Y 109/03001* (2013.01); *C12Y 111/01* (2013.01)

(58) Field of Classification Search
None
See application file for complete search history.

(56) References Cited

U.S. PATENT DOCUMENTS

| 5,801,022 A | 9/1998 | Navia et al. | |
| 6,218,581 B1 | 4/2001 | Nagaoka | |
| 7,303,892 B1* | 12/2007 | Adam | C07K 14/82 435/15 |
| 2002/0034802 A1* | 3/2002 | Karpusas | C07K 14/7055 435/183 |
| 2006/0142171 A1* | 6/2006 | Hatti-Kaul | C11D 3/386 510/320 |
| 2012/0064588 A1* | 3/2012 | Nagaoka | C12N 9/0004 435/155 |
| 2014/0150866 A1* | 6/2014 | Muguruma | B32B 17/10036 136/259 |
| 2016/0367558 A1* | 12/2016 | Oppenheimer | A61K 31/00 |

FOREIGN PATENT DOCUMENTS

| JP | 2001-19650 A | 1/2001 |
| JP | 2001-019650 A | 1/2001 |
| JP | 3294860 B | 6/2002 |
| JP | 3683129 B | 8/2005 |
| WO | WO 99/34010 | 7/1999 |
| WO | WO 2007/036235 A1 | 4/2007 |
| WO | 2010/134642 A1 | 11/2010 |
| WO | WO 2010/134642 A1 | 11/2010 |

OTHER PUBLICATIONS

De Groot (2006) Non-oxygen-forming pathways of hydrogen peroxide degradation by bovine liver catalase at low hydrogen peroxide fluxes, Free Radical Res., vol. 40, pp. 67-74.*
Lopez-Gallego et al. (2005) Co-aggregation of Enzymes and Polyethyleneimine: A Simple Method to Prepare Stable and Immobilized Derivatives of Glutaryl Acylase, Biomacromol., vol. 6, pp. 1839-1842.*
Kadinikova et al. (2002) Oxidation of ABTS by hydrogen peroxide catalyzed by horseradish peroxidase encapsulated into sol-gel glass. Effects of glass matrix on reactivity, J. Mol. Cataly., vol. 18, pp. 39-48.*
Colonna et al. (1992) Horseradish Peroxidase Catalysed Sulfoxidation is Enantioselective, J. Chem. Soc. Chem Comm., pp. 357-358.*
Office Action for European Patent Application No. 13853909.3 (dated May 3, 2016).
International Search Report for PCT/JP2013/080351 (dated Jan. 21, 2014).
Yamada et al., "Production of Useful Substances by Hybrid Process", Kagaku Zokan No. 119, Kagaku-Dojin Publishing Company, Inc., pp. 3-18, 49-60, 97-107 and 125-132 (Feb. 10, 1999).

(Continued)

*Primary Examiner* — Anand Desai
*Assistant Examiner* — Samuel Liu
(74) *Attorney, Agent, or Firm* — Merchant & Gould P.C.

(57) ABSTRACT

Provided are: a protein complex capable of selectively and asymmetrically oxidizing an enantiomer of a secondary alcohol without adding a coenzyme and having an asymmetric oxidation activity in a water-soluble solvent system in the presence of oxygen; a method for producing the same; and a method for coating the protein complex with a high molecular weight compound. The method for producing the protein complex includes: (1) enclosing a crude water-soluble protein in a gel, air-oxidizing the gel, and eluting the protein complex into an aqueous solution; and (2) applying gravity to concentrate and precipitate the protein complex, redissolving the precipitate in an aqueous glycine sodium hydroxide solution of about 0.5 mM and allowing the same to homogeneously coexist with a high molecular weight compound, and re-precipitating the solution and dehydrating and drying the same to yield a protein complex coated with a high molecular weight compound.

7 Claims, 18 Drawing Sheets

(56) References Cited

OTHER PUBLICATIONS

Fukui (ed.), "Bioreactor", Biotechnologies Series, Kodansha Scientific Ltd., pp. 1-75 (Mar. 1, 1985).
Chibata (ed.), "Immobilized Enzyme", Biotechnologies Series, Kodansha Scientific Ltd., pp. 1-8 (Mar. 20, 1975).
Morishige, "Development of Biocatalysts", Chemistry and Chemical Industry, The Chemical Society of Japan, vol. 62-1, pp. 44-45 (Jan. 2009).
Auld et al., "Medium- and short-chain dehydrogenase/reductase gene and protein families: The role of zinc for alcohol dehydrogenase structure and function", Cell. Mol. Life. Sci., 65(24):3961-3970 (2008).
Afolabi et al., "Site-Directed Mutagenesis and X-ray Crystallography of the PQQ-Containing Quinoprotein Methanol Dehydrogenase and Its Electron Acceptor, Cytochrome cL", Biochemistry, 40(33):9799-9809 (2001).
Zee et al., "Defects in cytochrome oxidase assembly in humans: lessons from yeast", Biochem. Cell. Biol., 84(6):859-869 (2006).
Putman et al, "Replacement of an Electron Transfer Pathway in Cytochrome c Peroxidase with a Surrogate Peptide," Biochemistry, 48(1):1-3 (2009).
Maruyama et al., "Poly(ethylene glycol)-lipase complexes that are highly active and enantioselective in ionic liquids," Org. Biomol. Chem., 2:1239-1244 (2004).
Urade, "Role of Table or Common Salt in Network Formation of Gluten Protein," Food and Technology, Japan Food Industry Association, Dec. 2008, pp. 1-9.
Watanabe, "Material Transformation Utilizing Protein Space: Molecular Design of Metalloenzyme, Mainly Heme Enzyme," Protein, Nucleic Acid and Enzyme, Kyoritsu Shuppan Co., Ltd., 49(14):2253-2259 (2004).
Thakur et al., "Enantioselective synthesis of (S)-α-arylpropionic acids via PD-catalyzed kinetic reduction of benzylic alcohols," Indian Journal of Chemistry, 44B:557-562 (Mar. 2005).
Stoimenova et al., "Nitrite-driven anaerobic ATP synthesis in barley and rice root mitochondria," Planta., 226(2):465-74 (Jul. 2007).
Abe et al., "Remarkable Activation of an Enzyme by (R)-Pyrrolidine-Substituted Imidazolium Alkyl Peg Sulfate," Adv. Synth. Catal., 350:1954-1958 (2008).
Hirakawa et al., "Construction of Artificial Enzyme Complexes Using Ring-Shaped Heterotrimeric Proteins, construction of Self-Sufficient Cytochrome P450," Kagaku to Seibutsu, The Japan Society for Bioscience, Biotechnology, and Agrochemistry, 51(8):521-523 (2013).
Guengerich, "Common and Uncommon Cytochrome P450 Reactions Related to Metabolism and Chemical Toxicity," Chem. Res. Toxicol., 14(6):611-650 (2001).
Miyamoto et al., "Biosynthesis Gene Cluster of Defense Response Substances Acquired by Plants, Control Mechanism of Phytoalexin Production in Rice," Chemistry and Biology, The Japan Society for Bioscience, Biotechnology, and Agrochemistry, 51(5):310-317 (2013).
Létoffé et al., "Functional Characterization of the HasAPF Hemophore and Its Truncated and Chimeric Variants: Determination of a Region Involved in Binding to the Hemophore Receptor," J. Bacteriol., 182(16):4401-4405 (Aug. 2000).
Krieg et al., "Heme uptake across the outer membrane as revealed by crystal structures of the receptor-hemophore complex," PNAS, 106(4):1045-1050 (Jan. 2009).
Nagaoka, "Cross-Linked Protein Complex Exhibiting Asymmetric Oxidation Activities in the Absence of Added Cofactor," Biotechnol. Prog., 28(4):953-961 (2012).

* cited by examiner

| Sample | Element analysis(wt%) | | | | |
|---|---|---|---|---|---|
| | C | H | N | S | O |
| PP | 48.83 | 8.56 | 12.76 | 1.78 | 6.06 |
| CLPC | 30.03 | 8.63 | 16.09 | 11.02 | 23.15 |
| PEG(1000)-PC | 46.04 | 8.34 | 6.92 | 1.59 | 10.85 |

(a)

(b)

(a)

(b)

(a)

(b)

(a)

(b)

(a)

(b)

(c)

(a)

(b)

(a) Flow for naproxen synthesis using Iron-binding protein complexcoated with polymer compound (HPC-coated PC)

(b) Conventional flow for naproxen synthesis

Figure. Large-scale synthetic process for (S)-naproxen by Syntex.
(See Harrington, P. J.; Lodewijk, E. Org. Process Res. Dev. 1997, 1, 72.)

(a)

(b)

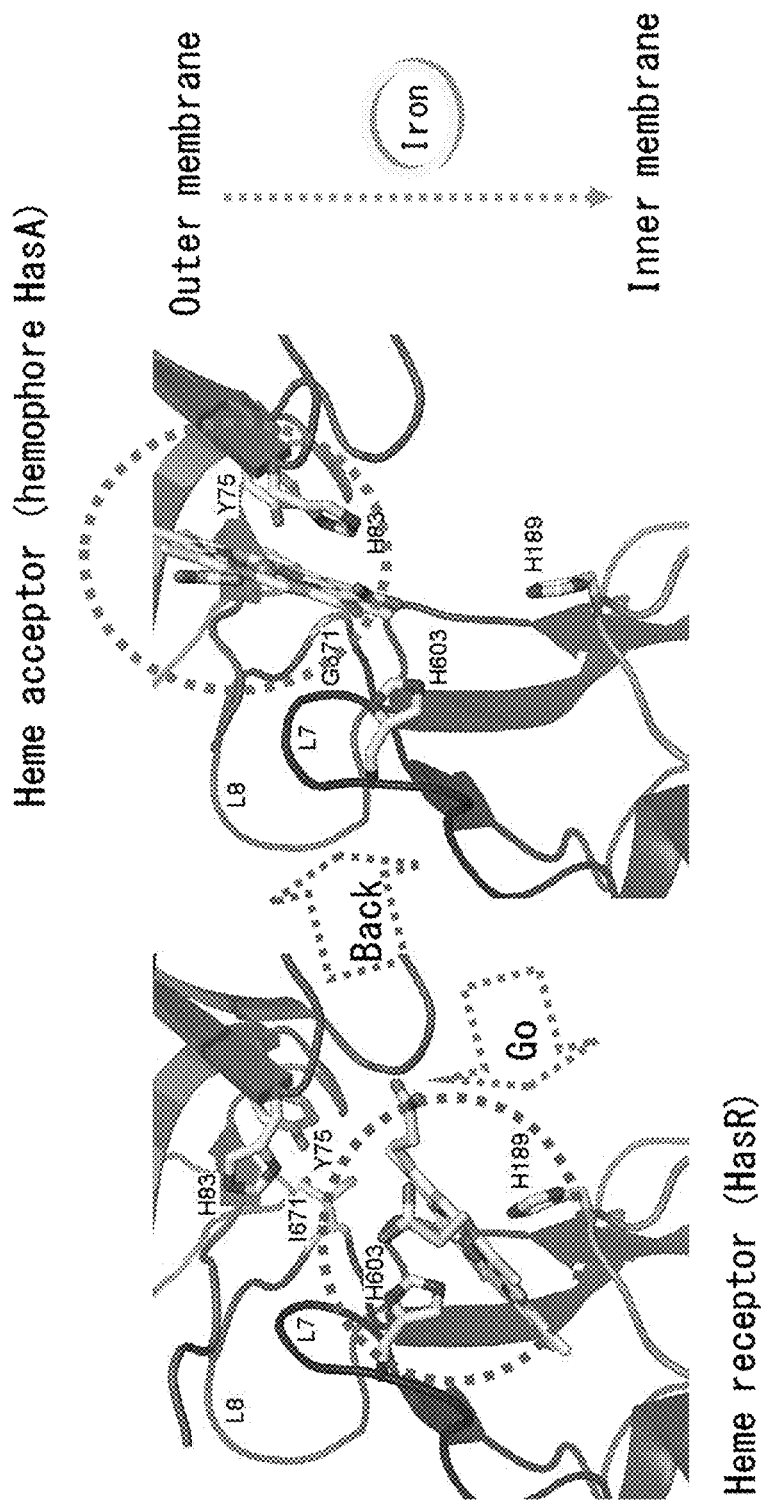

SEQUENCE LISTING

```
<160> NUMBER OF SEQ ID NOS: 3

<210> SEQ ID NO 1
<211> LENGTH: 33
<212> TYPE: PRT
<213> ORGANISM: Pseudomonas fluoroscens
<220> FEATURE:
<221> NAME/KEY: MISC_FEATURE
<222> LOCATION: (2)..(2)
<223> OTHER INFORMATION: Xaa is any amino acid
<220> FEATURE:
<221> NAME/KEY: MISC_FEATURE
<222> LOCATION: (9)..(9)
<223> OTHER INFORMATION: Xaa is any amino acid
<220> FEATURE:
<221> NAME/KEY: MISC_FEATURE
<222> LOCATION: (20)..(20)
<223> OTHER INFORMATION: Xaa is any amino acid
<220> FEATURE:
<221> NAME/KEY: MISC_FEATURE
<222> LOCATION: (23)..(23)
<223> OTHER INFORMATION: Xaa is any amino acid

<400> SEQUENCE: 1

Ser Xaa Ser Ile Ser Tyr Ser Thr Xaa Tyr Ala Thr Asn Thr Val Ala
1               5                   10                  15

Gln Tyr Leu Xaa Asp Trp Xaa Ala Tyr Phe Gly Asp Leu Asn His Arg
            20                  25                  30

Glu

<210> SEQ ID NO 2
<211> LENGTH: 34
<212> TYPE: PRT
<213> ORGANISM: Pseudomonas fluoroscens
<220> FEATURE:
<221> NAME/KEY: MISC_FEATURE
<222> LOCATION: (1)..(1)
<223> OTHER INFORMATION: Xaa is any amino acid or absent
<220> FEATURE:
<221> NAME/KEY: MISC_FEATURE
<222> LOCATION: (3)..(3)
<223> OTHER INFORMATION: Xaa is any amino acid or absent
<220> FEATURE:
<221> NAME/KEY: MISC_FEATURE
<222> LOCATION: (10)..(10)
<223> OTHER INFORMATION: Xaa is any amino acid
<220> FEATURE:
<221> NAME/KEY: MISC_FEATURE
<222> LOCATION: (21)..(21)
<223> OTHER INFORMATION: Xaa is any amino acid or absent
<220> FEATURE:
<221> NAME/KEY: MISC_FEATURE
<222> LOCATION: (24)..(24)
<223> OTHER INFORMATION: Xaa is any amino acid

<400> SEQUENCE: 2

Xaa Ser Xaa Ser Ile Ser Tyr Ser Thr Xaa Tyr Ala Thr Asn Thr Val
1               5                   10                  15

Ala Gln Tyr Leu Xaa Asp Trp Xaa Ala Tyr Phe Gly Asp Leu Asn His
            20                  25                  30

Arg Glu
```

```
<210> SEQ ID NO 3
<211> LENGTH: 205
<212> TYPE: PRT
<213> ORGANISM: Pseudomonas fluoroscens

<400> SEQUENCE: 3

Met Ser Ile Ser Ile Ser Tyr Ser Ala Thr Tyr Gly Gly Asn Thr Val
1               5                   10                  15

Ala Gly Tyr Leu Thr Asp Trp Ser Ala Tyr Phe Gly Asp Val Asn His
                20                  25                  30

Arg Pro Gly Glu Val Val Asp Gly Thr Asn Thr Gly Gly Phe Asn Pro
                35                  40                  45

Gly Pro Phe Asp Gly Thr Gln Tyr Ala Ile Lys Ser Thr Ala Ser Asp
        50                  55                  60

Ala Ala Phe Val Ala Asp Gly Asn Leu His Tyr Thr Leu Phe Ser Asn
65                  70                  75                  80

Pro Ser His Thr Leu Trp Gly Ser Val Asp Thr Ile Ser Leu Gly Asp
                85                  90                  95

Thr Leu Ala Gly Gly Ser Gly Ser Asn Tyr Asn Leu Val Ser Gln Glu
                100                 105                 110

Val Ser Phe Thr Asn Leu Gly Leu Asn Ser Leu Lys Glu Glu Gly Arg
                115                 120                 125

Ala Gly Glu Val His Lys Val Val Tyr Gly Leu Met Ser Gly Asp Ser
                130                 135                 140

Ser Ala Leu Ala Gly Glu Ile Asp Ala Leu Leu Lys Ala Ile Asp Pro
145                 150                 155                 160

Ser Leu Ser Val Asn Ser Thr Phe Asp Asp Leu Ala Ala Ala Gly Val
                165                 170                 175

Ala His Val Asn Pro Ala Ala Ala Ala Ala Asp Val Gly Leu Val
                180                 185                 190

Gly Val Gln Asp Val Ala Gln Asp Trp Ala Leu Ala Ala
                195                 200                 205
```

PROTEIN COMPLEX CAPABLE OF CATALYZING ASYMMETRIC OXIDATION REACTION AND METHOD FOR PRODUCING SAME

This application is a U.S. National Stage Application under 35 U.S.C. § 371 of International Patent Application No. PCT/JP2013/080351 filed 8 Nov. 2013, which claims the benefit of priority to Japanese Patent Application No. 2012-247945 filed 9 Nov. 2012, the disclosures of all of which are hereby incorporated by reference in their entireties. The International Application was published in Japanese on 15 May 2014 as WO 2014/073673.

TECHNICAL FIELD

The present invention relates to a protein complex which at least comprises iron, calcium and copper, and has activity that catalyzes an asymmetric oxidation reaction, and a process for producing the same.

The present application includes a Sequence Listing in electronic ASCII format as a text file entitled "Sequence Listing," which was created on Sep. 14, 2017 and has a size of 4,096 bytes. The Sequence Listing is hereby incorporated by reference in its entirety.

BACKGROUND

In various fields including the fields of pharmaceuticals and foods, there has been an increasing need for a technique for separating an optical isomer to thereby collect the one useful optical isomer. For example, research has been conducted on a process for producing drugs and perfumes by using an asymmetric hydrogenation (reducing) enzyme having a function of selectively oxidizing/reducing or deracemizing one of optical isomers.

A chemical change in vivo is usually catalyzed by an enzyme. A bioreactor is an example of one of the systems of utilizing such an action or mechanism of these enzymes in the production or analysis of useful substances.

An immobilized enzyme, which has been bonded to an insoluble carrier, plays a central role in a bioreactor. By use of the immobilized enzyme, a product can easily be separated from the enzyme serving as a catalyst. The immobilized enzyme has widely been used in the fields of research, medical care, analysis and industry. The central part of the bioreactor causing a chemical reaction is a reaction element, and a purified enzyme, organelle or cell per se is used for the purpose of converting a raw material into a product, or analyzing by utilizing a chemical change. Since the reaction element must remain in a reactor and be able to be used repeatedly, the reaction element is immobilized by various methods (with respect to details of utilization of these enzymes, for example, it is possible to refer to Non-Patent Document 1).

However, since the enzyme has numerous problems such as requiring extensive costs for purification and the purified enzyme often being unstable, there is still room for improvement. For this reason, there is an example wherein a microorganism containing the target enzyme was immobilized as is instead of the purified enzyme. Examples thereof may include an example wherein microorganisms containing aspartase were immobilized to produce L-aspartic acid, and an example wherein L-alanine was continuously produced by using aspartic acid able to be produced in this plant as a raw material (see, for example, Non-Patent Document 1 and Non-Patent Document 2).

As indicated in Non-Patent Document 3, with respect to a redox catalyst seen from an industrial point of view, it is considered that a method of utilizing functions per se of dehydrogenase and coenzyme, which are present in cells, such as microorganisms, yeasts and cultured plant cells, is superior in terms of cost, and that the excess cost burden required to isolate and purify oxidoreductase and coenzyme from boint is not worth the cost of an operation of stabilizing an enzyme, and conjugating a reaction (ketone→alcohol) with a reaction (coenzyme NADH→NAD$^+$) or a reverse reaction thereof.

A medium-chain dehydrogenase/reductase (MDR) type of alcohol dehydrogenase (ADS) is able to catalyze an oxidation reaction of a secondary alcohol using coenzyme NAD (H), and according to the review of Non-Patent Document 4, catalytic zinc, which acts as an electron transfer system, and structural zinc, which acts to maintain structure, are both present in this dehydrogenase, and regularity is observed in the amino acid sequence thereof at the locations of amino acids such as cysteine and histidine.

Since commercially available alcohol dehydrogenation (oxidation)/hydrogenation(reduction) enzymes are dependent on electron transfer between coenzymes produced by these microorganisms (NADH→NAD$^+$) and the intrinsic zinc, a reaction occurs by addition of coenzyme. An example of an enzyme product obtained by heat resistance treatment of a secondary alcohol dehydrogenase may be Secondary Alcohol Dehydrogenase A available from Thermostable Enzyme Laboratory Co., Ltd.

A process in which an asymmetric hydrogenase is used as is without being purified by a microorganism can be summarized as follows: 1) searching for and collecting a microorganism that induces a substrate transformation reaction, 2) culturing (for six months), and 3) carrying out a microbial reaction. Examples of problems encountered in this case may include: 1) burden in terms of time and costs required to find the microorganism and develop for practical application, and 2) requirement of the supervision of a specialist familiar with microbial procedures. Examples of problems associated with asymmetric hydrogenation (reduction) reactions using an organic metal catalyst (such as BINAP), for which there are many as 500,000 to 1,000,000 types, may include: 1) cost burden attributable to the reaction system in which hydrogen is pressurized in an organic solvent, 2) residual harmful metal (such as ruthenium) following the reaction, and 3) low stereoselectivity (85% ee to 95% ee in nearly all cases).

The merit of an asymmetric dehydrogenation (oxidation) catalyst is that it can play an auxiliary role in this conventional asymmetric technology. For example, an asymmetric dehydrogenation catalyst can be used for the purpose of selectively asymmetrically oxidizing and removing an unnecessary enantiomer produced with BINAP. An asymmetric oxidation catalyst in this case may preferably use a reaction system that 1) does not require the supervision of a specialist, 2) uses an aqueous medium, and 3) proceeds with low cost due to high stereoselectivity (100% ee).

Dehydrogenases involved in redox reactions have been reported that have iron, which has a broader range of electron mobility than zinc. For example, Non-Patent Document 5 reports a primary alcohol-specific dehydrogenase, specific for methanol or ethanol and the like, that has a quinoprotein as a coenzyme (which may also be referred to as "$CC_1$"). A general reaction formula of this PQQ-dehydrogenase is as indicated below, and oxygen supply is involved in the reaction.

$$4Fe^{2+}-CC_1+8H_{in}^{+}+O_2 \rightarrow 4Fe^{3+}-CC_1+2H_2O+\text{[Chemical Formula 1]}$$

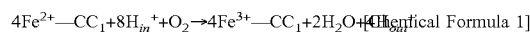

However, Non-Patent Document 5 does not report an asymmetric dehydrogenation reaction of a secondary alcohol in the presence of PQQ.

In addition, according to Non-Patent Document 6, a cytochrome oxidase (which may also be referred to as "$CC_2$") is reported in which the electron transfer of iron is involved.

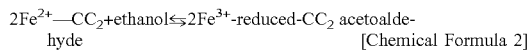
$$2Fe^{2+}\text{—}CC_2 + \text{ethanol} \leftrightarrows 2Fe^{3+}\text{-reduced-}CC_2 \text{ acetoaldehyde} \quad \text{[Chemical Formula 2]}$$

Although an enzyme is not involved in this reaction, there is no report in Non-Patent Document 6 of an asymmetric dehydrogenation reaction of a secondary alcohol in Non-Patent Document 6 in the same manner as PQQ.

According to Non-Patent Document 7, a peroxidase is reported in which the electron transfer of iron is involved (which may also be referred to as "$CC_3$").

$$H_2O_2 + CC_3\text{—}H_2 \rightarrow 2H_2O + CC_3 \quad \text{[Chemical Formula 3]}$$

An enzyme is also not involved in this reaction, and there is no report of an asymmetric dehydrogenation reaction of a secondary alcohol in Non-Patent Document 7 as well in the same manner as PQQ and cytochrome oxidase. The case of catalase, in which the electron transfer of iron is involved (which may also be referred to as "$CC_4$"), is similar in that an enzyme is not involved.

$$CC_4 + 2H_2O_2 \rightarrow CC_4 + O_2 + 2H_2O \quad \text{[Chemical Formula 4]}$$

In this manner, there are no known reports relating to an asymmetric dehydrogenase of a secondary alcohol based on the electron transfer of iron.

The invention of a novel asymmetric dehydrogenation (oxidation) catalyst that demonstrates an asymmetric dehydrogenation reaction of a secondary alcohol and is dependent on iron electron transfer and oxygen would make it possible to selectively asymmetrically oxidize and remove unnecessary enantiomers produced with BINAP. Moreover, since coenzyme NAD(P) is not present, it would be possible to realize a reaction system in which 1) the need for the supervision of a specialist is eliminated, while only requiring oxygen, 2) an aqueous medium is used, and 3) the reaction proceeds at low cost due to high stereoselectivity (100% ee).

Cytochrome P450 monooxygenase (P450) is further attracting attention with respect dependence on an iron electron transfer system and oxygen ($O_2$) and, dependence on a coenzyme (NAD(P) and/or FAD) depending on the case. According to Non-Patent Document 14, reduced iron was indicated to act on xenobiotic metabolism and the biosynthesis of secondary metabolites such as steroids, fatty acids, terpenoids or flovonoids by using oxygen atoms as oxidizing agent and catalyzing stereoselective and regioselective hydroxylation, epoxidation, dehalogenation and other oxidation reactions.

According to Non-Patent Document 15, P450 is formed for the purpose of acting by selecting different in molecules in all living organisms, and roughly 20 types have been identified in bacteria, roughly 60 types in animals, and several hundred types in plants. One reason of this large number of types in plants is that it is the result of having been avariciously acquired to a greater degree than in other living organisms as a result of developing, evolving and adapting in a specific environment as indicated in Non-Patent Document 16.

According to Non-Patent Document 17, a hemophore is an iron-capturing protein intrinsic to iron-binding protein, and is described as being widely present in pyrroloquinoline quinone-alcohol dehydrogenase (PQQ-ADD), cytochrome oxidase and P450 localized in membrane protein, and in peroxidase, catalase and ABC transporter.

Patent Document 1 indicates an example wherein an optically active alcohol was resolved at an optical purity of about 100% ee from a crude protein derived from animals and plants, and an optically active alcohol (100% ee, yield: 50%) is synthesized by combining a first step for extracting a water-soluble protein from grains or beans, a second step for encapsulating the protein in a calcium alginate gel, and a third step for carrying out an asymmetric oxidation conversion reaction of a substrate using the encapsulated protein as a catalyst. In addition, in Patent Document 2, an optically active alcohol (100% ee) is synthesized by combining a first step for extracting a water-soluble protein selected from egg white and ovalbumin separated from egg white, a second step for encapsulating the protein in calcium alginate, and a third step of carrying out an asymmetric oxidation conversion reaction of a substrate using the encapsulated protein as a catalyst.

Moreover, Patent Document 3 discloses a production process wherein, after having encapsulated a water-soluble protein from grains or beans in in calcium alginate gel and oxidizing in air, a protein fraction eluted in warm water is precipitated with ammonium sulfate, chemically modified with glutaraldehyde and formed into a powder, and the resolution/synthesis of an optically active alcohol using that process.

In addition, according to Non-Patent Document 8, a PEG-coated lipase complex (white powder) is obtained by coating lipase with polyethylene glycol (PEG) and forming an emulsion by adding toluene followed by subjecting to freeze-drying treatment for 24 hours. Moreover, an asymmetric acylation reaction of alcohol in an ionic liquid ([Bmin][PF6]) has been studied, and a dramatic improvement in catalyst activity was reported to be observed as a result of coating with PEG (IL1-PS: Non-Patent Document 13).

The size of the lipase hydrolase market in the chemical industry is considered to be small in comparison with the asymmetric hydrogenation market relating to BINAP catalyst and microbial hydrogenation, being only ¹/₁₀₀ to ¹/₁₀₀₀ the size of that market, while the size of the asymmetric redox market is large. Thus, a technology for coating PEG onto a certain asymmetric oxidase instead of lipase would be deeply interesting in terms of the market. This PEG-coated oxidase would be able to function as a cocatalyst that may preferably remove unnecessary enantiomers formed in BINAP reactions. However, existing PEG coating treatment requires the consumption of a large amount of toluene, and has concerns over economic and environmental burdens. Therefore, there is a strong desire for a coating technology that does not use an organic solvent (such as toluene) that results in such concerns over economic and environmental burdens.

Typical examples of methods used to produce an immobilized enzyme may include:

(1) a carrier binding method wherein the extracted and purified enzyme is bound to a water-insoluble carrier such as a derivative of a polysaccharides such as cellulose, dextran or agarose or a polyacrylamide gel;

(2) a chemical modification method wherein the extracted and purified enzyme is immobilized by forming a chemically modified bond between the extracted and purified enzymes using a reagent having two or more functional groups; and (3) a (microcapsule type) encapsulating method wherein the extracted and purified enzyme is incorporated in a fine matrix of a gel such as alginate, starch, konjak (devil's tongue jelly), polyacrylamide gel or polyvinyl alcohol, or coated with a semitransparent film.

In general, the significance of these immobilized enzymes is that they may be preferably recovered (and more preferably, recovered and then reused) after reacting. Although treatment involving encapsulation in calcium alginate gel followed by oxidizing in air as described in Patent Document 3 is an example of a novel technology that further advances this immobilization technology by oxidizing an immobilized biomaterial in air to transform to a beneficial material, definitive evidence has yet to be observed regarding the estimated mechanism of this treatment with respect to the formation of a disulfide bond and/or reduction of iron molecules in a hemophore (iron-capturing protein) accompanying air oxidation of cysteine within a protein, and the change of the PC per se to water solubility resulting in a "exudation" effect simultaneous to an "asymmetric oxidation" effect.

PRIOR ART DOCUMENTS

Patent Documents

Patent Document 1: Japanese Patent No. 3,294,860
Patent Document 2: Japanese Patent No. 3,683,129
Patent Document 3: International Publication No. WO 2010/134642

Non-Patent Documents

Non-Patent Document 1: Yamada et al. "Production of Useful Substances by Hybrid Process," *Kagaku Zokan No.* 119 (Kagaku-Dojin Publishing Company. Inc. 1999): and Fukui, "Bioreactor," *Biotechnologies Series* (Kodansha Scientific Ltd. 1985)
Non-Patent Document 2: Biotechnologies Series, Kodansha Ltd., "Immobilized Enzyme", edited by Ichirou Chibata, Kodansha Scientific Ltd.
Non-Patent Document 3: "Chemistry and Industry (i.e., Kagaku To Kogyo)", Vol. 62-1, January 2009, pp. 44-45
Non-Patent Document 4: "Cell Mol. Life Sci., 64 (2008) 3961-3970", (The role of zinc for alcohol dehydrogenase structure), D. S. Auld, et al.
Non-Patent Document 5: "Biochemistry 40 (2001), 9799-9809", (Site-directed mutagenesis and X-ray crystallography of the PQQ-containing quinoprotein methanol dehydrogenase and its electron acceptor, cytochrome cL), Afolabi, et al.
Non-Patent Document 6: "Biochem. Cell. Biol. 84 (2006), 859-869", (Defects in cytochrome oxidase assembly in humans: Lessons from yeast.), Zee, J. M., et al.
Non-Patent Document 7: "Biochemistry 48 (2009), 1-3", (Replacement of an electron transfer pathway in cytochrome c peroxidase with a surrogate peptide), Hays Putnam, et al.
Non-Patent Document 8: "Org. Biomol. Chem." No. 2, pp. 1239-1244 (2004), (Poly(ethylene glycol)-lipase complex that are highly active and enantioselective in ionic liquid), "Gotoh, et. al., Kyushu University"
Non-Patent Document 9: "Food and Technology (i.e., Shokuhin To Gijutshu)", December, pp. 1-9 (2008) (Role of Table or Common Salt in Network Formation of Gluten Protein), "Reiko Urade; Graduate School of Agriculture, Kyoto University"
Non-Patent Document 10: "Protein, Nucleic acid, Enzyme" 2004, November, Vol. 49, No. 14, —Molecular Design of Metalloenzyme, Mainly Heme Enzyme— (Graduate School of Science, Nagoya University; Yoshihito Watanabe)
Non-Patent Document 11: "—Enantioselective synthesis of (S)-α-arylpropionic acid via Pd-catalyzed kinetic resolution of benzylic alcohols—", (Vinay V. Thakur; from Chemical Engineering & Process Development Division, National Chemistry Laboratory, India)
Non-Patent Document 12: "Planta" 226 (2), pp. 465-74 (July 2007), "Nitrite-driven anaerobic ATP synthesis in barley and rice root mitochondria", "Stoimenova, M. et al."
Non-Patent Document 13: "Adv. Synth. Catal.", 350, pp. 1954-1958 (2008), "Remarkable Activation of an Enzyme by (R)-Pyrrolidine-Substituted Imidazolium Alkyl PEG Sulfate", "Yoshikazu Abe, et al."
Non-Patent Document 14: "Chemistry and Biology", Vol. 51, No. 8, pp. 521-523 (2013), "Construction of Artificial Enzyme Complexes using Ring-Shaped Heterotrimeric Proteins, Construction of Self-Sufficient Cytochrome P450", "Hidehiko Hirakawa, et al. (Research Department, Graduate School of Engineering, Tokyo University)"
Non-Patent Document 15: (d) Guengerich, *Chem. Res. Toxicol.*, 14(6):611-650 (2001)
Non-Patent Document 16: "Chemistry and Biology", Vol. 51, No. 5, pp. 310-317 (2013), "Biosynthesis Gene Cluster of Defense Response Substances Acquired by Plants, Control Mechanism of Phytoalexin Production in Rice", "Koji Miyamoto, et al. (Biological Production Engineering Research Center, Tokyo University)"
Non-Patent Document 17: "J. Bacteriol." 182(16), pp. 4401-4405 (2000), "Functional Characterization of the HasAPF Hemophore and its Truncated and Chimeric Variants: Determination of a Region involved in Binding to the Hemophore Receptor", "Sylvie Letoffe, et al."
Non-Patent Document 18: "PNAS" 106(4), pp. 1045-1050 (2009), "Heme uptake across the outer membrane as revealed by crystal structures of the receptor-hemophore complex", "Stefanie Krieg, et al."

DISCLOSURE OF THE INVENTION

Problems to be Solved by the Invention

An object of the present invention is to provide a protein complex having activity that catalyzes an asymmetric oxidation reaction under mild conditions while overcoming the above-mentioned drawback of the prior art.

Another object of the present invention is to provide a protein complex that is superior in terms of environmental aspects, safety and cost, and a preferable process for producing that protein complex.

Means for Solving the Problems

As a result of conducting extensive studies, the inventor of the present invention found a protein complex having activity that catalyzes an asymmetric oxidation reaction. More specifically, the inventor of the present invention found that at least the presence of iron is intimately involved in catalyst activity when the protein complex of the present invention is used as a catalyst of an asymmetric oxidation reaction, and further found a protein complex that contains more iron, has fewer impurities and has higher catalyst activity than protein complexes obtained in the prior art, as well as a process for producing that protein complex.

Effects of the Invention

Characteristics of the present invention may include, for example, the following four points.

(a) The present invention does not fall under a microbial genetic resource as related to the Convention on Biological Diversity (CBC), participated in by 193 countries, including Japan, and enacted on Dec. 29, 1993, and the Nagoya Accord relating to Access and Benefit-Sharing of Microbial Genetic Resources of December 2010.

(b) The present invention effectively uses unused biological resources (biomass) produced from higher plants/higher animals.

(c) The present invention is a protein complex that has accomplished genetic development and retains an iron electron transfer system in the presence of oxygen, and has asymmetric dehydrogenation activity on secondary alcohol.

(d) The protein complex is a protein complex that retains a plurality of iron-binding proteins (enzyme), including catalase.

Thus, according to the present invention, a protein complex is provided that has a function that cannot be compensated for by microbial resources, and asymmetric dehydrogenation activity on secondary alcohol produced only in higher plants/higher animals.

According to the present invention as previously explained, a plant-derived protein complex and/or an animal-derived protein complex are provided that have been imparted with activity that catalyzes a practical asymmetric oxidation reaction.

According to the present invention, the protein complex of the present invention (to be referred as PC) can be further provided in the form of a protein complex coated with a polymer compound that is environmentally-friendly and realizes low-cost production by a preferable production process relating to forming this type of animal/plant-derived protein complex into a powder.

BRIEF DESCRIPTION OF THE DRAWINGS

FIGS. 11(a) and 11(b) are examples of graphs indicating effects on polymer compounds and the activity thereof during HPC-PC production, while FIG. 11(c) is an example of a graph indicating an example of the effects of continuous addition of racemic 1-(2-naphthyl) ethanol (to be referred to as Rac-2) as substrate.

FIGS. 15(a) and 15(b) are examples of schematic diagrams showing the locations of disulfide bonds, calcium, pyrroloquinoline quinone (PQQ) at the active sites of (a) cytochrome C oxidase and (b) PQQ-ethanol dehydrogenase.

FIG. 21 is an example of a schematic diagram showing a state wherein a cell membrane hemophore (iron-capturing protein) transfers iron to HasR (transfer protein) following iron capture, and again returns the iron to a fixed position.

BEST MODE FOR CARRYING OUT THE INVENTION

Figure 1:
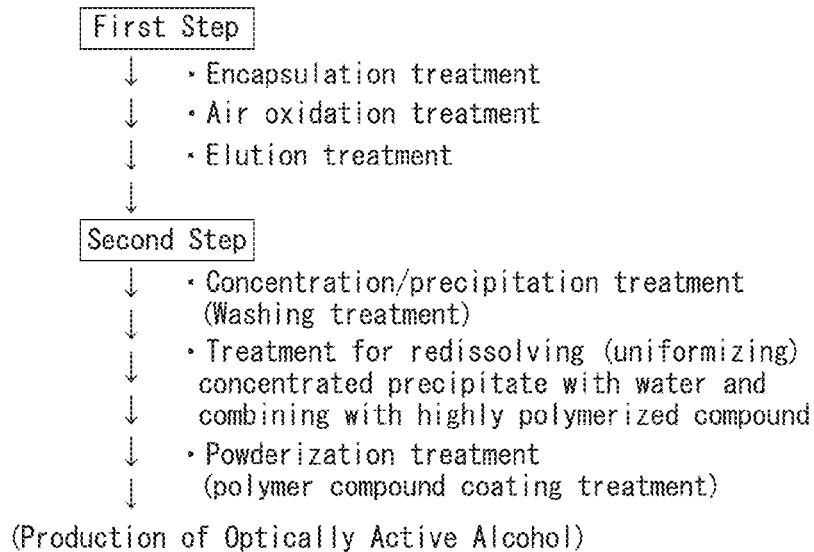
FIG. 1 is a conceptual diagram representing one aspect of a process for producing a protein complex coated with a polymer compound (to be referred to as HPC-PC).

The following provides a more detailed explanation of the present invention while referring to the drawings as neces- (Production of Polymer Compound-Coated Protein Complex (HPC-PC))

The following provides a description of a process for producing a polymer compound-coated protein complex in a preferable aspect of the present invention.

In this aspect, a process for producing a polymer compound-coated protein complex (HPC-PC) is characterized in that it comprises a first step, which consists of encapsulating treatment in which gel beads are obtained by encapsulating an animal/plant-derived water-soluble crude protein in a gel, air oxidation treatment in which the gel beads are oxidized in air, and elution treatment in which a protein complex (PC) suspension is obtained by eluting the air-oxidized gel beads into an aqueous solution; and, a second step, which consists of concentration treatment in which a protein complex is precipitated by applying gravity to the protein complex suspension, followed by combining the protein complex precipitate with a polymer compound in an aqueous solution and then subjecting to freeze-drying (FD) treatment to obtain a polymer compound-coated protein complex.

(First Step: Encapsulation Treatment)

In this aspect, in the encapsulation treatment, an animal/plant-derived water-soluble crude protein is first encapsulated in a gel to obtain a hydrophobic carrier.

Here, the animal/plant-derived water-soluble crude protein (PC) refers to a crude protein obtained from an animal and/or plant, and a commercially available product may be used or that obtained by extracting directly from an animal resource and/or plant resource may be used. An example of a commercially available product may be green pea protein available from Organo Foodtech Corp. (trade name: Green Pea Protein PP-CS).

Examples of such plant resources may include grains such as buckwheat, amaranthus, rice, wheat, barley, corn, oats, rye, chestnuts, Japanese millet, barnyard millet, adlay or sorghum, beans such as adzuki beans, kidney beans, green peas, mung beans or soybeans, and seeds, leaves, stems, roots, flowers, fruit and other plant tissue thereof, including common grasses and weeds. A process such as that disclosed in Patent Document 1 can be suitably used to extract crude protein from a plant resource.

Moreover, although examples of animal resources may include those derived from chicken eggs as egg white or ovalbumin, poultry, amphibian or fish egg albumin can be used in the same manner, the animal resource is not limited to that derived from chicken eggs and the origin of the protein is not limited to eggs. A process such as that disclosed in Patent Document 2 can be suitably used to extract crude protein from an animal resource.

Although specific examples of methods used to obtain the biological material-encapsulated gel may include encapsulation methods consisting of incorporating in a fine matrix of an alginate, starch, konjak (devil's tongue jelly), polyacrylamide or polyvinyl alcohol gel (matrix type) and coating with a semitransparent film, in terms of obtaining a protein complex from an animal resource, an encapsulation method using calcium alginate is inexpensive and environmentally-friendly, and may be most preferable from the viewpoint of ease of the encapsulation and recovery procedures.

More specifically, an encapsulated crude protein (gel) can be obtained, for example, by dissolving an animal/plant-derived water-soluble crude protein in distilled water, followed by adding an aqueous sodium alginate solution and stirring until homogeneous, and dropping an aqueous calcium chloride solution into the resulting mixture of crude protein and sodium alginate. Here, the concentration of the aqueous calcium chloride solution may preferably be 50 mM or more.

(First Step: Air Oxidation Treatment)

In a preferable aspect of the present invention, in air oxidation treatment, the above-mentioned gel is oxidized by allowing to stand undisturbed in air. The ultimately obtained protein complex of the present invention can be obtained at high yield by carrying out the air oxidation treatment for 30 minutes or more, preferably for 3 hours or more and even more preferably for 5 hours or more. This air oxidation treatment results in an "aqueous solution exudation effect", by which sulfur oxide, formed as a result of a single cysteine of the amino acid components of the crude protein bonding with oxygen (S=O and/or S—O), and/or an iron atom in a hemophore (iron-capturing protein), are reduced causing the PC per se to change to water solubility, while simultaneously resulting in an "effect that causes elution of protein complex having activity that catalyzes an asymmetric oxidation reaction (such as mitochondria)". Thus, air oxidation treatment is essential as the key to the process for producing the protein complex of the present invention.

The air oxidation process of the crude protein-encapsulated gel may be preferably carried out at 30° C. or lower, and more preferably by being careful to suppress bacterial growth by treating at 20° C. or lower. Although treatment is required to be carried out promptly until warm water extraction, in cases when avoidably necessary, the encapsulating gel can be refrigerated in the vicinity of 10° C. to 4° C. In this case, however, it becomes increasingly difficult to prevent deterioration of activity level.

(First Step: Elution Treatment)

In a preferable aspect of the present invention, elution treatment is carried out to obtain a protein complex by eluting the air-oxidized biological material-encapsulated gel with an aqueous solution. Shaking or stirring the gel beads in water may be preferable for the eluting means. The water may preferably be warm water, and the water temperature may preferably be 30° C. to 50° C. The number of times the gel beads are shaken can be suitably determined within a range in which the gel beads move back and forth. The shaking time may preferably be 20 hours or more and may more preferably be 30 hours or more. A constant-temperature shaking incubator or a temperature-controlled stirring tank and the like can be used for the stirring means.

Although a characteristic sulfur odor begins to be generated as elution of the protein complex (PC) from the gel proceeds and bacterial growth cannot be prevented during the process of warm water extraction at 30° C. to 40° C., the concentration (centrifugation) procedure and FD drying procedure may be preferably carried out promptly by the time the sulfur odor changes to a putrid odor. If bacterial growth is left unchecked until the production of a putrid odor, this can lead to 1) a decrease in activity level, and 2) a loss of stereoselectivity. Although the gel can also be refrigerated in the vicinity of 10° C. to 4° C. to prevent the production of a putrid odor, a decrease in the activity level thereof cannot be prevented.

(Second Step: Concentration Treatment)

In a preferable aspect of the present invention, concentration treatment is carried out for the purpose of removing impurities remaining in the aqueous solution and obtaining a concentrated precipitate of the protein complex by applying gravity to the protein complex suspension obtained in the above-mentioned first step. Examples of means for achieving this may include a method consisting of further physically applying a strong gravitational force to the precipitate, which was obtained by gravity precipitation by allowing to stand naturally, with a centrifuge to remove the aqueous solution fraction and obtain a concentrated protein complex (PC) having asymmetric oxidation activity. It is not necessary to limit the method used to centrifugal separation provided the method enables the protein complex to be concentrated rapidly.

The function of the protein complex (PC) obtained in this concentration treatment can be activated by adding 5 equivalents of 50 mM glycine NaOH buffer (pH 9.0 to pH 10.0) based on the amount of precipitate for the purpose of further enhancing purity and concentrating, and the PC can also be simultaneously washed by subjecting to centrifugal separation several times. Washing treatment can be carried out by adding 50 mM glycine NaOH buffer to the precipitate of the protein complex obtained by concentration treatment and redissolving, followed by adding applying gravity and removing the aqueous solution fraction to remove impurities in the form of water-soluble low molecular weight compounds. On the other hand, concentration of the target highly polymerized protein may be preferably carried out using field flow fractionation (FFF).

(Second Step: Polymer Compound Coating Treatment)

In a preferable aspect of the present invention, in the polymer compound coating treatment, the precipitate of the protein complex obtained in the above-mentioned concentration treatment is in co-presence with a polymer compound in an aqueous solution followed by preferably coating by vacuum freeze-drying (FD). Coating results in the demonstration of 1) an effect that improves thermostability, 2) an effect that maintains stereoselectivity, and 3) an effect that improves ease of the reaction procedure. Thus, in the case of not coating, since both enantiomers of a secondary alcohol are easily oxidized, the yield of optically active alcohol (maximum 50% yield) decreases dramatically or results in the optically active alcohol not being obtained. Thus, polymer compound coating treatment of the protein complex is indispensable to the production process of the present invention.

Examples of the above-mentioned polymer compound that can be used in the present invention may include polyethylene glycol (PEG), carboxymethyl cellulose (CMC) and α-starch. Among these, Since PEG is highly water-soluble and is able to coat the protein complex precipitate with a smaller amount than other polymer compounds, it demonstrates superior productivity. In addition, since all raw materials of α-starch for producing the protein complex are edible in comparison with other polymer compounds, it can be used in a nutritional supplement able to be administered orally.

The concentration of the above-mentioned aqueous solution of the polymer compound can be suitably determined according to the scale of the production equipment and the chemical species of the polymer compound used. In the case of using PEG for the polymer compound, PEG may be preferably used at 0.2% by weight, or at a concentration of 0.5% to 1.0%, based on the weight of the protein complex obtained in the above-mentioned concentration treatment. For example, a protein complex that retains a preferable activity level can be processed by redissolving with PEG (5.0±0.5 g) per 500 L of an aqueous solution of PEG and 50 mM glycine NaOH buffer (pH 9.0 to pH 10.0) based on 100 g±10 g for the weight of the protein complex precipitate, followed by vacuum freeze-drying (FD).

Although the polymer compound and protein complex have asymmetric oxidation activity when both are present in an aqueous solution, since a decrease in activity level cannot be avoided accompanying a transition from a sulfur odor to a putrid odor as bacterial growth progresses, it is necessary to promptly carry out powderization treatment for enhancing storageability and fluidity on the solution.

(Second Step: Powderization Treatment)

In a preferable aspect of the present invention, a polymer compound-coated protein complex (powder) is obtained from a state in which a polymer compound and a protein complex are both present in the above-mentioned aqueous solution followed by subjecting to drying and dehydration treatment to carry out powderization treatment. Examples of means for processing into a powder may include vacuum freeze-drying, hot-air drying, press drying, compression drying and air drying. Among these, vacuum freeze-drying may be preferable since moisture can be completely removed in a short period of time. In the case of carrying out vacuum freeze-drying, after freezing at about −50° C. for one hour or more, and preferably after completely freezing, a vacuum is drawn inside the system and the temperature is raised to about 50° C. to sublimate the moisture. Furthermore, compression drying can also be carried out after freezing an aqueous solution of the above-mentioned polymer compound-coated protein complex in advance followed by storing for several days. However, there are cases in which activity level may decrease in the case of storing the combined solution frozen for one week or more.

The dried polymer compound-coated protein complex (HPC-PC) can be converted to a catalyst that expresses activity that catalyzes an asymmetric oxidation reaction while being in the form of a powder that can be stored at normal temperature by carrying out crushing with a ball mill and the like.

(Protein Complex)

In a preferable aspect of the present invention, the protein complex (PC) of the present invention is characterized in that, it is a protein complex that at least contains iron, and in an FT-IR spectrum thereof, has at least one peak in the region of 1085±50 cm$^{-1}$, in a fraction having the most potent asymmetric oxidation activity, an amino acid sequence from the N-terminal to the 33rd amino acid has the sequence S*SISYST*YATNTVAQYL*DW*AYFGDLNHRE (SEQ ID NO: 1), exhibits prominent foaming in a reaction with hydrogen peroxide, and releases oxygen.

Figure 3:
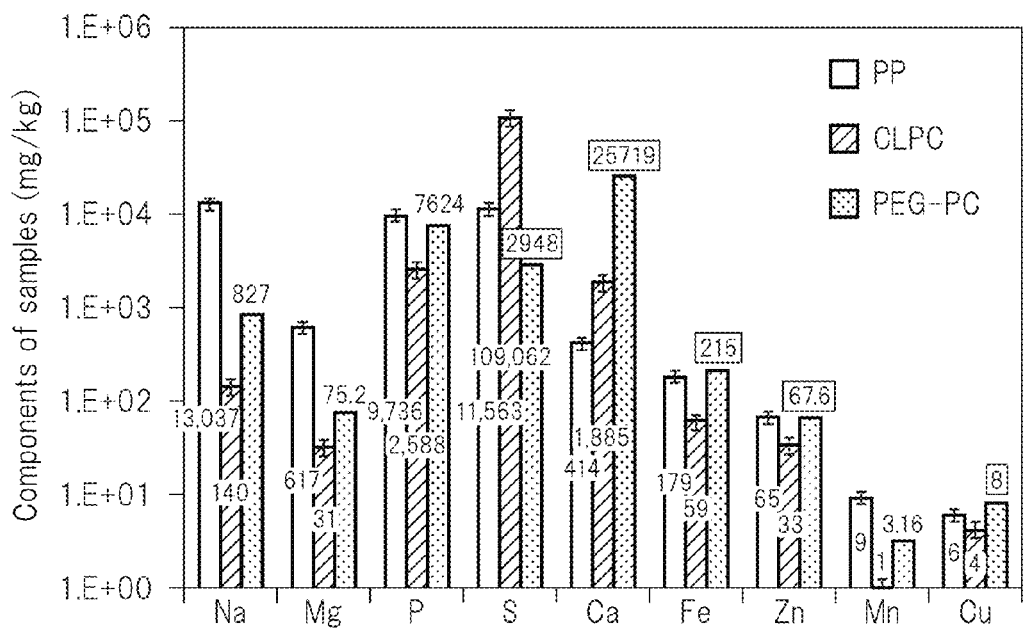
FIG. 3 is an example of a graph and table of the results of a constituent element analysis of a processed PC (CLPC and HPC-PC).

FIG. 3 is graph indicating the results of analyzing the inorganic elements and organic elements of (i) pea protein (PP), (ii) chemically-modified protein complex (CLPC), and (iii) PEG-coated protein complex (PEG-PC) for the purpose of investigating the residual ratios of raw materials of a processed PC (CLPC and PEG-PC). Analysis of inorganic elements was carried out with an ICP emission analyzer, while organic elements were analyzed by suitably using ion chromatography system or elemental analyzer and the like. The PEG-PC of the present invention has an iron concentration that is four times greater than CLPC, while the calcium content has been increased to about 20 times that of CLPC.

Figure 8:
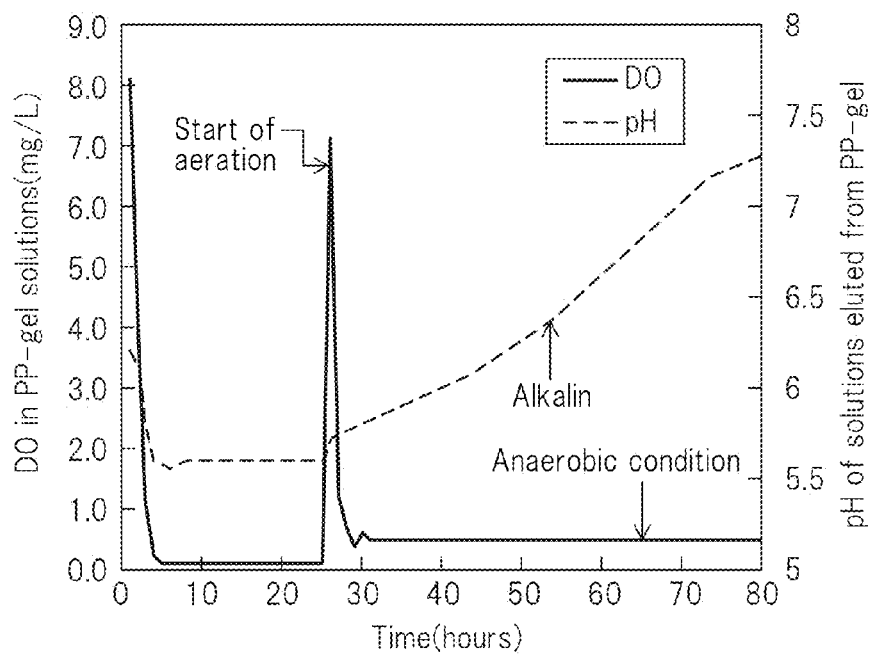
FIG. 8 is an example of a graph indicating changes in DO and pH when PC is eluted from green pea protein-encapsulated gel and changes therein when oxygen was supplied 24 hours later.

Although FIG. 8 indicates a state in which the protein complex dissolves into an aqueous solution from air-oxidized pea protein gel in the first step, the pH of the aqueous solution can be seen to gradually shift towards the alkaline side. The reason for this is that, as shown in FIG. 3, the protein complex not only contains iron ions (which act to transfer electrons in an oxidation reaction), but also contains a large amount of calcium that acts to maintain conformation, and these cations are presumed to cause the pH of an aqueous solution of the protein (PC) to shift towards the alkaline side.

PC is a cationic protein composed of iron involved in electron transfer and a large amount of calcium that acts to maintain three-dimensional conformation. Thus, as indicated in Patent Document 1 and Patent Document 2, even the PC suspension indicated in the first step of FIG. 1 retains asymmetric oxidation activity. In the case of CLPC indicated in Patent Document 3, the three-dimensional structure is chemically maintained (immobilized) by chemical modification with glutaraldehyde. (Furthermore, redissolving of the concentrated precipitate with water in the second step of FIG. 1 may preferably be redissolving of the concentrated precipitate with glycine buffer (pH 9 to pH 10)). The HPC-PC has a physical polymer compound coating (immobilized), and combines the functions of shifting the aqueous solution towards the alkaline side and the maintaining of conformation by calcium. The reason for the aqueous medium system indicated in Table 10 having activity is thought to be attributable to these two functions.

As shown in FIG. 3 and Table 1, since PEG-PC does not contain ammonium sulfate in comparison with CLPC, as shown in Table 11, asymmetric oxidation activity and catalase activity are four times stronger. CLPC is subjected to ammonium sulfate precipitation treatment in the second step, and activity is thought to weaken as a result of 10% or more of this ammonium sulfate remaining even after chemical modification and FD drying and causing a decrease in the concentration of active protein.

FIG. 4(a) indicates the raw material residual ratios (see Table 1) of processed PC (CLPC and PEG-PC). The graph indicates the results of FT-IR analyses on (i) pea protein (PP), (ii) polyethylene glycol (PEG), (iii) PEG-PC (Sanyo Catalyst 1), (iv) PEG-PC treated with 30% ammonium sulfate (Sanyo Catalyst 2), and (v) sodium alginate. FIG. 4(b) indicates a graph of the results of FT-IR analyses on (i) pea protein (PP), (ii) CLPC (Sanyo Catalyst 8_64_2011), and (iii) sodium alginate carried out for the same purpose.

Based on the results of FIGS. 4(a) and 4(b), the detected amount of PEG-PC (Sanyo Catalyst 1) was extremely low or not detected for a peak of 1300 cm$^{-1}$ to 1500 cm$^{-1}$ indicating the residual amount of sodium alginate in comparison with PEG-PC (Sanyo Catalyst 2) and CLPC (Sanyo Catalyst 8_64_2011). Namely, in the case of PEG-PC (Sanyo Catalyst 1) that does not use ammonium sulfate, the effect is demonstrated of not allowing ammonium sulfate to remain, but also not allowing the raw material sodium alginate to remain.

On the basis of the above, as shown in Table 1, the HPC-PC production process has the effect of preventing ammonium sulfate and the raw material sodium alginate from remaining in advance, thereby resulting in a four-fold improvement in activity. A process was able to be found that enables iron-binding protein to be preferably concentrated from pea protein.

Furthermore, the at least one peak present in the region of 1085±50 cm$^{-1}$ is a peak indicating a sulfur oxide derived from ammonium sulfate or disulfide bonds (S=O and/or S—O), and in this case, can be a peak that enables confirmation of the "exudation effect" and the "effect that causes elution of protein complex having activity that catalyzes an asymmetric oxidation reaction" resulting from air oxidation of amino acid cysteine.

FIG. 5(a) is a graph showing a state of gel filtration chromatography on PC contained in a supernatant fraction following centrifugal separation in the first step, while FIG. 5(b) is a graph summarizing the results of HPLC after adding the substrate rac-2 (0.8 mM) to the fractionated solution (3 mL aliquots) followed by allowing to react for 48 hours. The most potent asymmetric oxidation activity is observed for No. 36.

In FIG. 5(a), the upper plot indicates a supernatant obtained after centrifugal separation of the PC suspension in the first step, the middle plot indicates a 4% pea protein powder solution, and the lower plot indicates a molecular weight marker solution. The graph summarizes results obtained by injecting each sample into a gel filtration chromatograph following ultrafiltration. The supernatant fractions were fractionated in 3 mL aliquots collected from the gel filtration chromatography in 60 vials.

Figure 6:
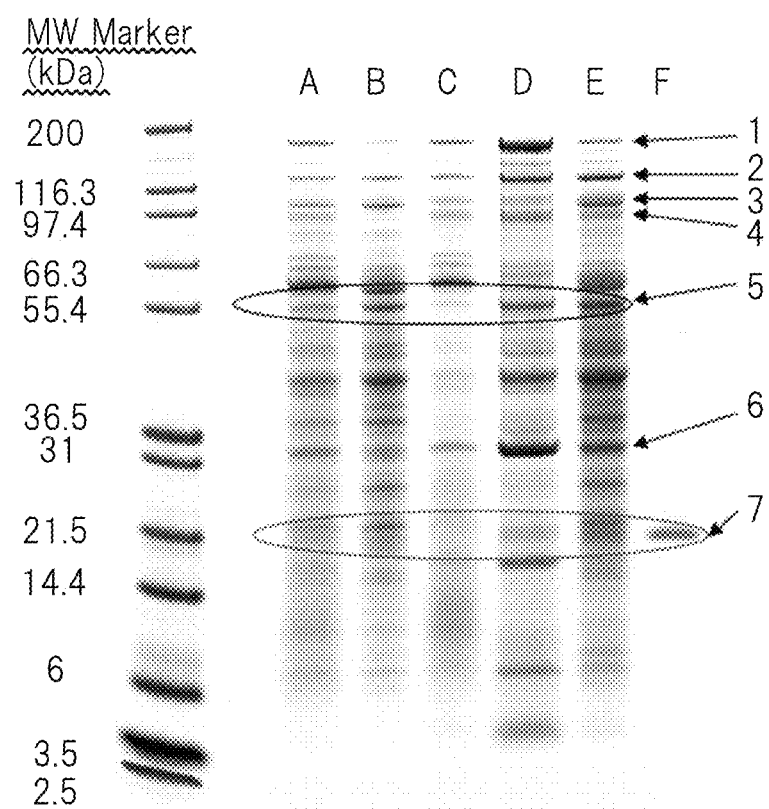
FIG. 6 is a photograph showing an example of SDS-PAGE results of one aspect of each fraction (A to E) obtained by centrifugally separating an aqueous solution of a PC obtained in a Step 1 and of Fraction No. 36 (F) obtained by gel filtration chromatography.

FIG. 6 indicates the results of SDS-PAGE for sample NO. 36 (F), for which potent activity was confirmed, and other samples A to E. More specifically, sample A is a suspension of the protein complex (PC) obtain in the first step, sample B is a solution obtained by redissolving a precipitate obtained after centrifuging sample A with five equivalents of 50 mM glycine NaOH buffer (pH 9.0 to pH 10.0), sample C is a supernatant fraction obtained following centrifugation of sample B, sample D is a solution obtained by redissolving a precipitate obtained by centrifugal separation after adding 30% (w/v) of ammonium sulfate to sample A, and sample E is a solution obtained by redissolving a precipitate obtained by centrifugal separation after adding 30% (w/v) of ammonium sulfate to sample B. As a result, an extremely dark, single band appeared in the vicinity of a molecular weight of 20 kDa in the fraction of No. 36 (F) for which potent asymmetric oxidation activity was confirmed.

Moreover, the dark, single band was cut out of the gel and subjected to N-terminal sequence analysis with a protein sequencer for the purpose of identifying the protein. As a result, the amino acid sequence from the N-terminal of the band protein was identified to the 33rd residue. The resulting amino acid sequence was S*SISYST*YATNTVAQYL*DW*AYFGDLNHRE (SEQ ID NO: 1), and all amino acid sequences of the hemophore (iron-capturing protein) of "YP 262445.1" that matched this amino acid sequence with 93% homology in a BLAST query sequence analysis are as shown in Table 3.

Figure 7:
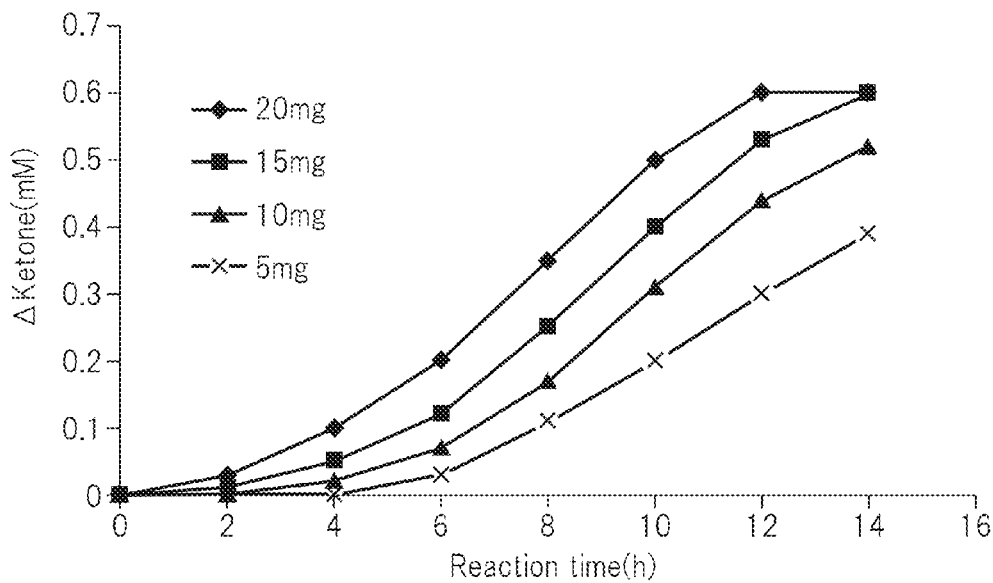
FIGS. 7(a) and 7(b) are examples of graphs of deriving HPC-PC activity level (units/g per hour) using racemic 6-metoxy-1-(2-naphthyl) ethanol (to be referred to as Rac-1) as substrate.
Figure 7:
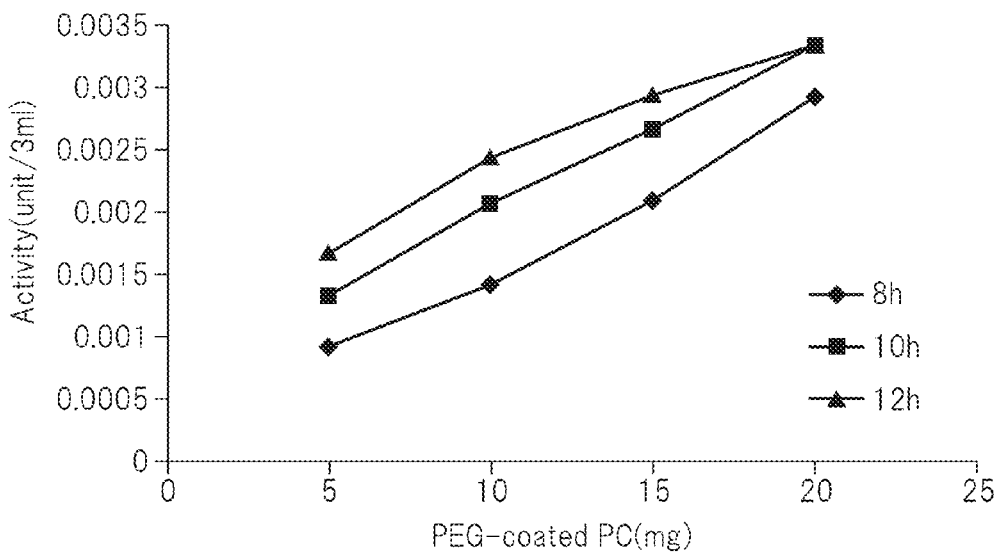

FIG. 7(a) indicates the results of reacting PEG-PC containing the iron-binding protein (5 mg to 20 mg) under conditions of a temperature of 40° C. and using Rac-1 (1.2 mM) as substrate in an aqueous medium system (4 mL) by plotting ketone formation on the vertical axis and plotting reaction time (2 hour intervals) on the horizontal axis. FIG. 7(b) is a graph in which activity level (units/mg per hour) obtained using a calculation formula {amount of ketone formed (mM)÷reaction time} is plotted on the vertical axis and the amount of PEG-PC is plotted on the horizontal axis.

Based on the results of FIG. 7(b), specific activity calculated according to instantaneous velocity was 15 units/g per hour to 36 units/g per hour. In addition, specific activity similarly calculated according to average velocity at a reaction time of 12 hours was 14 units/g per hour. Furthermore, in the present invention, units refer to units of enzyme activity, and 1 unit is equal to the amount of enzyme capable of converting 1 μmole of substrate per hour (units: μmol/h). In addition, "specific activity" indicates enzyme activity per unit substrate weight. The specific activity per 1 g of enzyme is expressed in units/g.

PEG-PC also has catalase activity in addition to asymmetric oxidation activity. Catalase is a substance that releases oxygen by reacting with hydrogen peroxide ($H_2O_2$). When 15 g of the PEG-PC of the present invention having a particle diameter of 50 μm is placed in a test tube having a diameter of 18 mm followed by the addition of 1.0 mL of 5% hydrogen peroxide, about 0.2 cm to 3.5 cm of bubbles are formed by generation of oxygen. Furthermore, as shown in Table 11, the height of the bubbles is proportional to the iron concentration of the PC, and a proportional correlation can be confirmed with the duration of the asymmetric oxidation reaction in a comparison with CLPC.

(Process for Producing Optically Active Alcohol)

In a preferable aspect of the present invention, a process for producing an optically active alcohol is characterized by allowing HPC-PC to act on a racemic alcohol serving as a substrate and selectively obtaining one of the enantiomers of the racemic alcohol.

In addition, a process for producing an optically active alcohol is also provided by the present invention that is characterized by selectively obtaining the other enantiomer not involved in the reaction by selectively asymmetrically oxidizing the other enantiomer of the racemic alcohol to a ketone.

(Estimated Mechanism)

According to findings of the inventor of the present invention, in a preferable aspect of the present invention, a preferable animal/plant-derived protein complex (PC) is estimated to be provided due to the reasons indicated below.

As a result of encapsulating an animal/plant-derived crude protein of an inexpensive biological material in a calcium alginate gel, an environment can be obtained in which the crude protein can be oxidized in air in the presence of calcium, and as a result thereof, (i) a PC undergoes a change in the properties thereof to become water-soluble in a form that is led to form disulfide bonds within the protein and/or a form in which an iron molecule within a hemophore (iron-capturing protein) is reduced causing the PC per se to become water-soluble (ii) the PC that has been subjected to cations results in an aqueous solution thereof shifting to the alkaline side, and (iii) the PC that induces an asymmetric oxidation reaction may be preferably eluted and purified by simply shaking in warm water.

The presence of dissolved Ca salt and oxygen eluted in warm water promotes the formation of disulfide bonds among amino acid cysteine between molecules of pea protein (PP) and the like, or in other words, promotes a change to water solubility accompanying formation of sulfur oxide (S=O and/or S—O), thereby assisting so as to be able to be easily extracted in warm water. The reasons for the improvements in catalyst activity and yield of the PC are that the gel may be preferably oxidized in air and that "exudation" is facilitated at suitable dissolved oxygen and Ca ion concentrations when dissolving in warm water.

In the production process of the present invention, the PC may be preferably obtained by taking advantage of the properties of this "exudation effect" accompanying air oxidation of the animal/plant protein, and its accompanying "effect that causes elution of PC having activity that catalyzes an asymmetric oxidation reaction", and as a result of this "reverse thinking", in which the objective is to preferably change the PC having activity that catalyzes an asymmetric oxidation reaction to water solubility instead of the objective of immobilization by calcium alginate gel, the production process of the present invention is characterized by effectively extracting a PC that acts in the manner of an enzyme at low cost while being environmentally-friendly.

(Estimated Mechanisms of Related Documents)

Examples of documents that support the "estimated mechanism" of the present invention as previously described may include the documents indicated below.

In Non-Patent Document 9, table salt and calcium chloride are known to have an effect that causes gladin and glutenin to change a property such that they dissolve in water by changing their interaction with gluten protein (water solubility effect), and an effect that causes intermolecular distance to be shortened by strengthening the interaction between gluten composite proteins (aggregating effect).

With respect to the effect of shortening intermolecular distance (aggregating effect), although the intermolecular distance of gluten is 7.7 Å in the absence of the addition of salt, in the case of adding salt, intermolecular distance has been shown to be shortened to within 6.4 Å. Since the intermolecular distance between histidine and iron in an active domain of myoglobin mutant is 5.7 Å, the effect of designing a suitable arrangement of a functional amino acid residue of the active domain can also be expected to be an aggregation effect attributable to addition of salt (Non-Patent Document 10).

Moreover, in the case of having produced a protein component (glutenin and gliadin) of wheat flour dough in the presence of table salt, the addition of table salt has been reported to cause a change in the intermolecular distance between protein molecules, causes the protein component to become insoluble in pure water, and causes the protein component to change to a property that demonstrates water solubility in saltwater.

In addition to the formation of disulfide bonds accompanying air oxidation, the amino acid cysteine also contributes to maintaining the conformation of oxygen by bonding with metals such as Ca, Fe or Zn. In this case, the significance of encapsulating in calcium alginate gel is the result of "reverse thinking", which takes advantage of the "exudation effect", resulting from the formation of sulfur oxide (S=O and/or S—O) accompanying air oxidation of amino acid cysteine contained in animal/plant protein and/or the reduction of iron molecules within a hemophore (iron-capturing protein) and a change in the PC per se to water solubility, and the resulting "elution of PC having activity that catalyzes an asymmetric oxidation reaction", and is characterized by effectively extracting a PC that has activity that catalyzes an asymmetric oxidation reaction at low cost while being environmentally-friendly.

(Various Studies)

The following describes various studies relating to HPC-PC in a preferable aspect of the present invention.

(Various Studies: Constituent Element Analysis of Protein Complex (CLPC, PEG-PC) of the Present Invention)

Figure 4:
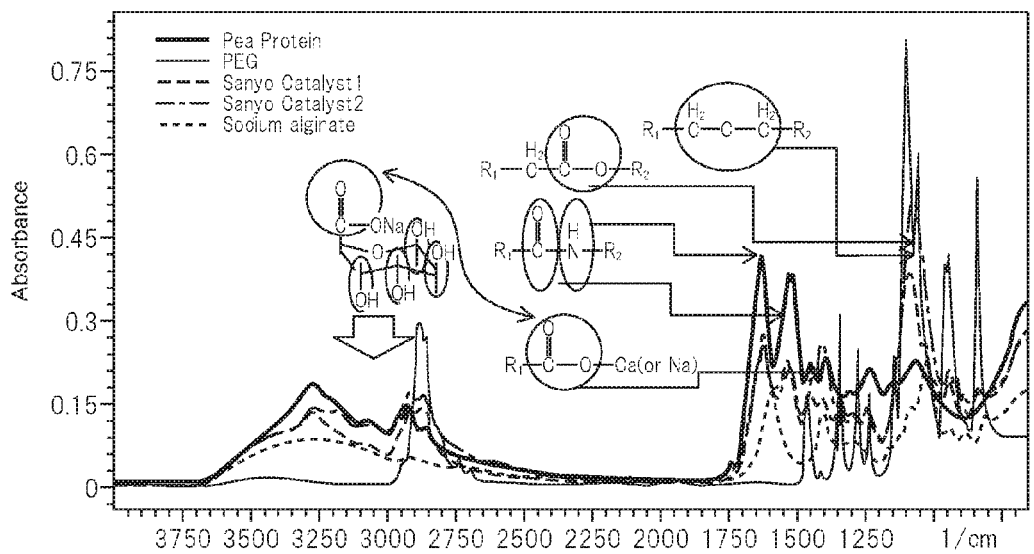
FIGS. 4(a) and 4(b) are graphs indicating examples of the results of FT-IR of a processed PC (CLPC and HPC-PC) and raw materials thereof.
Figure 4:
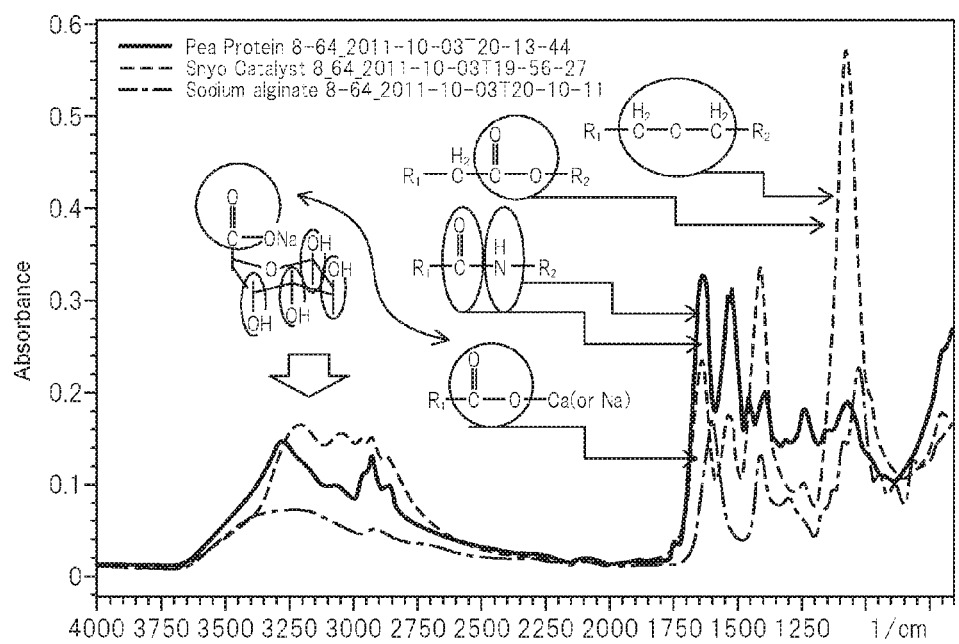

Detailed information based on the constituent elements of processed PC powder in the form of CLPC and HPC-PC is obtained from FIGS. 3 and 4 and Tables 1 and 11. First, in a comparison between CLPC and PEG-PC, the activity levels were 48 hours for CLPC and 13 hours for PEG-PC, with that of CLPC being about four times greater, while the iron contents were 59 ppm for CLPC and 215 pm for PEG-PC, with that of PEG-PC being about four times greater, thereby suggesting that an iron-binding protein lies at the core of the asymmetric oxidation activity of the present invention. An example of an iron electron transfer-based enzyme is cytochrome oxidase indicated in Non-Patent Document 6 and FIG. 15(a), and is reported to oxidize ethanol to aldehyde. Cytochrome oxidase fulfills the role of a regulator of electron transfer of iron ions (FIG. 15(a)).

Moreover, according to Non-Patent Document 5, another example of an iron electron transfer-based enzyme is PQQ-containing quinoprotein methanol dehydrogenase as shown in FIG. 15(b). However, there are no reports relating to asymmetric oxidation of secondary alcohol in either of these iron electron transfer systems, while only electron transfer between zinc and NAD(P) retained by cysteine (Cys) indicated in Non-Patent Document 4 (formula shown below) has been confirmed to be an example of a redox reaction in the prior art.

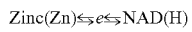 [Chemical Formula 5]

Thus, the asymmetric dehydrogenation reaction attributable to an enzyme-dependent iron electron transfer system of the present invention provides a novel process that does not require the addition of coenzyme.

(Various Studies: FT-IR Analysis of Protein Complex (CLPC and HPC-PC) of the Present Invention)

FIGS. 4(a) and 4(b) indicate the results of a detailed examination of the degree of contamination of raw materials in the form of pea protein (PP) and sodium alginate for PEG-PC (Sanyo Catalyst 1: no addition of ammonium sulfate) and CLPC (Sanyo Catalyst 8_64_2011: addition of ammonium sulfate). As a result thereof, as shown in Table 1, the residual amounts of sodium alginate and ammonium sulfate were able to be nearly completely removed in the PEG-PC (Sanyo Catalyst 1) process that does not use ammonium sulfate, thereby confirming that a target iron-binding protein can be preferably concentrated from PP.

As shown in Table 11, the activity of PEG-PC is four times stronger than that of CLPC (48 hours as compared to 13 hours), and the iron content is four times more concentrated (concentrated from 59 ppm to 215 ppm).

(Various Studies: Protein Identification in Fraction having Potent Activity)

Based on the results of gel filtration chromatography, SDS-PAGE on the active fraction thereof, and subsequently the results of N-terminal sequence identification of the single band with a protein sequencer along with BLAST query sequence analysis, the enzyme involved in PC activity was identified to be an iron-binding protein {93% query coverage: HasAp gene product [*Pseudomonas fluorescens* Pf-5]}. The molecular weight is 20.853 Da, and this coincided with the results of SDS-PAGE for the active fraction No. 36.

Figure 20:
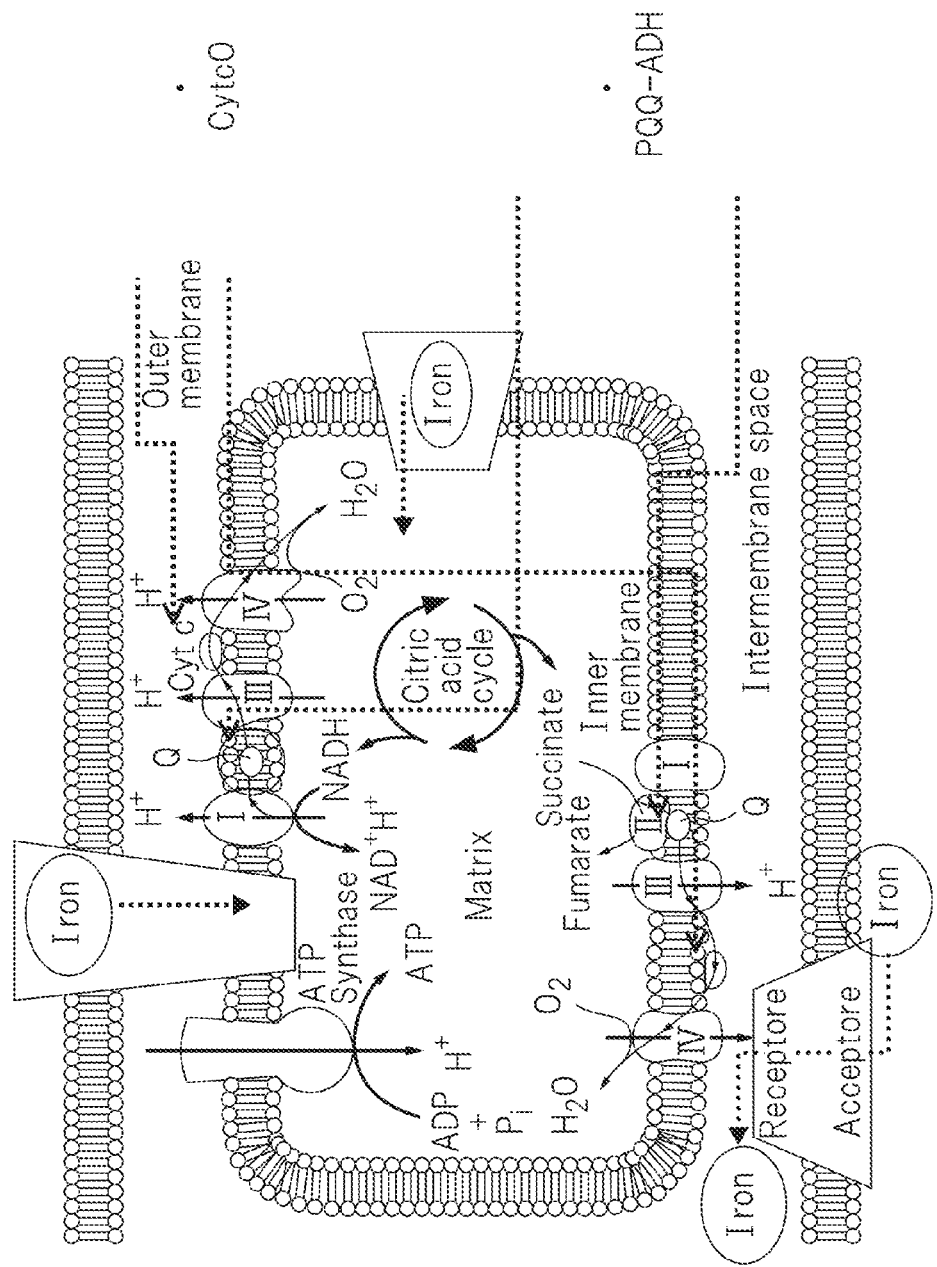
FIG. 20 is an example of a schematic diagram showing an electron transfer chain of an oxidative phosphorylation site in mitochondria.

The results of identifying the protein attributable to the characteristic dark band on SDS-PAGE by MARDI-TOF and LC-MSMS are shown in Table 4. With respect to protein related to succinic acid-producing microorganisms of Band 3, based on the results of the ATP-binding cassette (ABC) transporter family of band 5 with respect to protein, PC is derived from a membrane protein of intracellular tissue such as mitochondria (which includes iron-binding enzymes, including catalase), and was presumed to be able to be preferably concentrated by centrifugation due to the high molecular weight thereof. FIG. 20 introduces a citric acid cycle and electron transfer system that contain intramitochondrial complex I (Complex I). PQQ-dehydrogenase having an iron electron transfer system (Non-Patent Document 5: PQQ-ADH, shown in FIG. 15(b)) and cytochrome oxidase (Non-Patent Document 6: CytcO, shown in FIG. 15(a)) are present here. FIG. 21 is an example of a schematic diagram showing an electron transfer chain at the site of oxidative phosphorylation in mitochondria.

(Various Studies: Activity Inhibition Test of CLPC Asymmetric Oxidation Reaction by Addition of Additive)

Since PC having activity that catalyzes an asymmetric oxidation reaction is an enzyme in the manner of PQQ-dehydrogenase having an iron electron transfer system (Non-Patent Document 5) and cytochrome oxidase (Non-Patent Document 6), it would first be worthwhile to confirm whether or not it is subjected to thermal denaturation and chemical modification. As a result, evidence was obtained indicating that it is enzyme as shown in Table 6.

Moreover, on the basis of Table 7, PC is deactivated by the addition of 1 mM of chelating agent or aqueous $ZnCl_2$ solution, thereby obtaining evidence that oxygen is based on the iron electron transfer system of ([Chemical Formula 1]) or ([Chemical Formula 2]).

On the basis of the above, PC was able to be determined to be an iron-binding protein that is PQQ-dehydrogenase retaining an iron transfer (indicated by the formulas of (Chemical Formula 1) and/or (Chemical Formula 2)) (Non-Patent Document 5) and cytochrome oxidase (Non-Patent Document 6).

The iron-binding protein can be easily concentrated and precipitated by oxidizing in air in the manner of the first step shown in FIG. 1 followed by eluting in warm water as a membrane protein containing iron-binding enzyme, including catalase, and finally subjecting to centrifugal separation. The precipitate is then in co-presence with a polymer compound in warm water and subjected to FD treatment to process into HPC-PC powder having enhanced storageability, resulting in a catalyst that is able to catalyze asymmetric oxidation of secondary alcohol.

HPC-PC is an electron transfer system dependent on oxygen and iron that does not require the addition of cofactor NAD(P) or selection of buffer or pH conditions. It allows an optically active alcohol to be easily obtained by a stirring procedure in an aqueous medium and in the presence of oxygen (uncapped) (Example 13 and Table 10).

HPC-PC enables a naproxen precursor (S-1, >99% ee) to be synthesized from Rac-1. The pharmaceutical "naproxen" can be easily synthesized in accordance with Non-Patent Document 11. The organic synthesis process for synthesizing from S-1 is an organic synthesis system (yield: 83%, 92% ee) consisting of (1) bromination (—Br) of a hydroxyl group (—OH), (2) conversion to a nitrile form (—CN), and (3) conversion to a carboxylic acid (—COOH).

Figure 17:
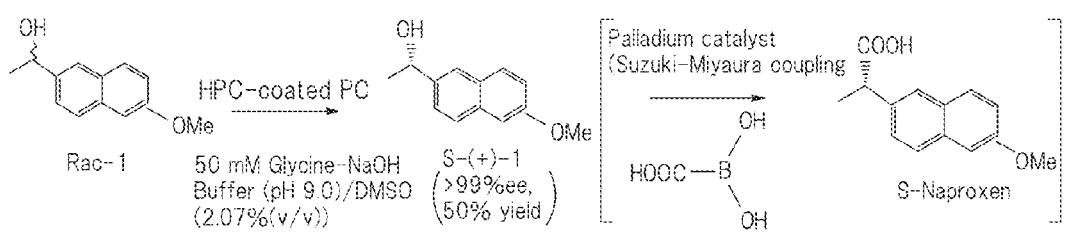
FIGS. 17(a) and 17(b) are examples of schematic diagrams showing synthesis of a naproxen precursor and synthesis of naproxen using the protein complex of the present invention, and an example of a schematic diagram showing a conventional naproxen synthesis process.
Figure 17:
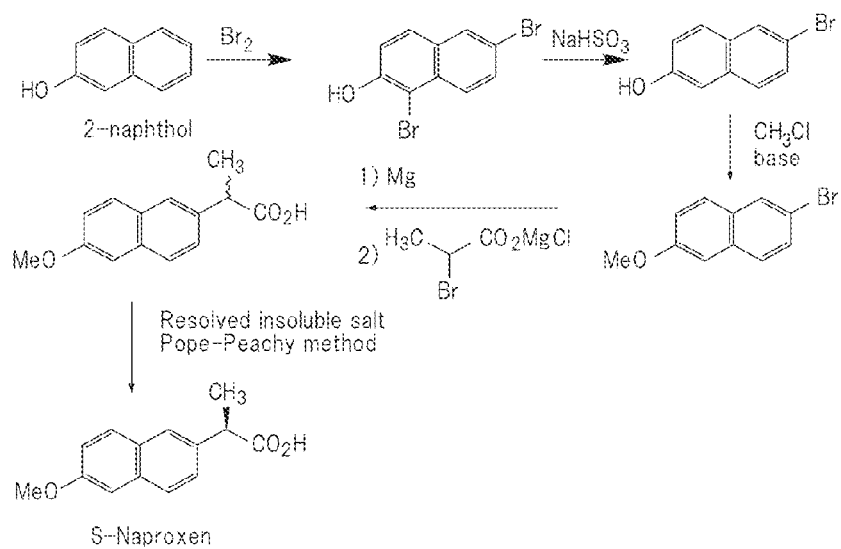
Figure 18:
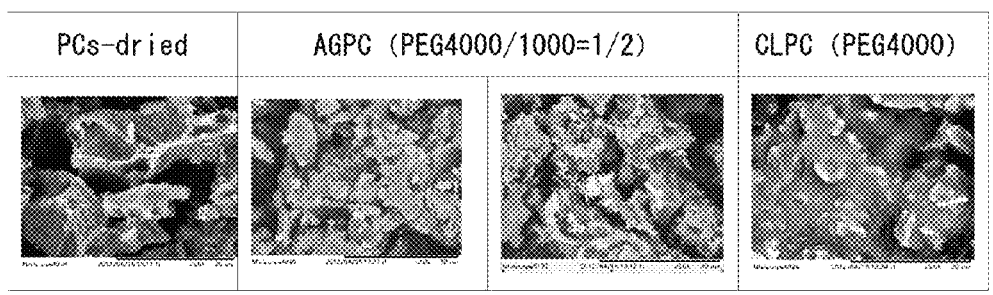
FIG. 18 indicates microscopic images of the surface of PCs-dried (uncoated) and the surface of PC coated with 2.6% $Ca^{2+}$ by CLPC (PEG-MW: 4000) and AGPC (PEG-MW: 4000/1000=1/2) coating.

FIG. 17(b) shows a flow chart of a conventional process used to synthesize naproxen. Naproxen is an organic compound that is classified as an aromatic carboxylic acid, and is a type of non-steroidal anti-inflammatory drug (NSAID) used as an analgesic, antipyretic and anti-inflammatory agent.

The PC of the present invention can be presumed to be a membrane protein derived from a cell organelle, and particularly from mitochondria, as described below, and is thought to be a membrane protein having an iron electron transfer chain function based on the cytochrome C oxidase reaction formula of [Chemical Formula 2] shown in FIG. 15(a) and the PQQ-ethanol dehydrogenase reaction formula of [Chemical Formula 1] shown in FIG. 15(b).

FIG. 16(a) shows the flow of Step 1. PC having the functions of PQQ-ethanol dehydrogenase and cytochrome C oxidase, may be preferably eluted from an air-oxidized alginate gel-encapsulated biological material, and after immobilizing to HPC-PC, carries out an asymmetric oxidation reaction on various secondary alcohols due to the action of the iron electron transfer system (Chemical Formula (6)).

FIG. 16(b) indicates the action of ATP synthase in the citric acid cycle in which PQQ-ethanol dehydrogenase and cytochrome C oxide are linked, and the production of energy (ATP) (Non-Patent Document 12).

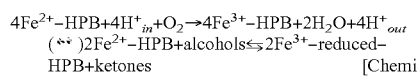 [Chemical Formula 6]

Animal/plant-derived protein encapsulated in calcium alginate gel may preferably induce air oxidation in the presence of calcium salt and oxygen following air oxidation. At least one peak appearing in the region of 1085±50 cm-1 obtained by FT-IR measurement indicates intermolecular disulfide bonds (sulfur oxide: S=O and/or S—O) within the protein, and this causes a change to water solubility while at the same time generating the effect of the protein complex having activity that catalyzes an asymmetric oxidation reaction (membrane protein which includes iron-bonding enzymes, including catalase) being eluted in warm water.

The composition of the protein complex indicated in the present invention is a membrane protein that contains (1) an iron-binding protein involved in electron transfer, and (2) a large amount of calcium that retains the conformation of that enzyme, has an iron electron transfer system in the form of catalase as well as a chain reaction of cytochrome C oxidase and PQQ-dehydrogenase as oxidation functions, and is characterized by a dehydrogenation reaction of secondary alcohol in the presence of oxygen. Thus, the present invention provides a reaction system that is clearly different from conventional redox enzyme ([Chemical Formula 15]).

Moreover, there are two types of PC consisting of that which has an S-selective oxidation reaction and that which acts on R-selective oxidation. As indicated in Table 12 and Table 13, the PC indicated in the present invention is able to use different biological materials in the first step, and produces two types of enantiomers having different stereoselectivity. Thus, both enantiomers (R-isomer and S-isomer) can be synthesized by using the PC according to these two types.

On the basis of the above, in comparison with conventional secondary alcohol dehydrogenase of an electron transfer system using zinc and cofactor (NAD(P) and FAD), which includes bothersome and labor-intensive oxygen purification and isolation steps, this finding provides an asymmetric organic synthesis reagent that allows an optically active alcohol (yield: 50%, 99% ee or more) to be effectively obtained with high selectivity that is also superior in terms of cost and ease of the procedure since the asymmetric oxidation reaction 1) does not require the addition of cofactor (NAD(H) or FAD), 2) is an oxygen-dependent asymmetric oxidation reaction, 3) is an extremely mild reaction system in an aqueous medium that is not dependent on pH, and 4) enables both enantiomers to be used separately.

(Measurement of Catalase Activity—1)

As was previously described, the iron-containing complex of the present invention has catalase activity in addition to asymmetric oxidation activity. This catalase activity has the property of releasing oxygen by reacting with hydrogen peroxide ($H_2O_2$) as previously mentioned. Catalase activity can be preferably evaluated according to the level of "bubble formation" based on generation of oxygen when 15 mg of the PEG-PC of the present invention having a particle diameter of 50 μm is placed in a test tube having a diameter of 18 mm and adding 1.0 mL of 5% hydrogen peroxide (also refer to Table 11 to be subsequently described).

It is only required to be able to visually confirm bubble formation based on generation of oxygen with the naked eye in order to confirm the level of bubble formation. More specifically, the level of bubble formation (and/or height of bubbles formed in the test tube) may preferably be 2 mm or more. Moreover, the height of bubble formation may be more preferably 5 mm or more (and even more preferably 8 mm or more and particularly preferably 10 mm or more).

(Measurement of Catalase Activity—2)

On the other hand, catalase activity can also be preferably evaluated by measuring the amount of hydrogen peroxide consumed in the above-mentioned reaction (refer to Table 14 and Table 15 to be subsequently described).

More specifically, as will be indicated in the examples to be subsequently described, the residual amount of hydrogen peroxide following the reaction can be measured using "Pack Test" available commercially from Kyoritsu Chemical-Check Lab Corp. This measurement method can be preferably used, for example, to screen candidate substances.

(Measurement of Catalase Activity—3)

Moreover, as will be indicated in the examples to be subsequently described, the residual amount of hydrogen peroxide following the reaction can be measured with a commercially available digital hydrogen peroxide concentration meter, and specific activity of the PEG-PC or CLPC of the present invention with respect to a hydrogen peroxide decomposition reaction can be measured based on that measurement.

In the case of using a digital hydrogen peroxide concentration meter, the specific activity of the iron-containing protein complex of the present invention with respect to a hydrogen peroxide composition reaction (the amount of PEG-PC able to decompose 1 μM $H_2O_2$ in the reaction for 5 minutes in 2 mM hydrogen peroxide (1 mL) serving as substrate) may preferably be 200 μg and may be more preferably 150 μg (and particularly preferably 130 μg). The unit in this case in an aspect in which the iron-containing protein complex of the present invention is PEG-PC is such that the specific activity with respect to the hydrogen peroxide decomposition reaction (amount of PEG-PC able to decomposition 1 μM $H_2O_2$) may preferably be 100 μg and may more preferably be 80 μg (and particularly preferably 60 μg).

(Selective Asymmetric Oxidative Synthesis of Both Enantiomers by PEG-PC)

Finally, inversion of the active center of the PC can be promoted by coating a PC precipitate obtained in the step of FIG. 1 with low molecular weight polyethylene glycol (PEG molecular weight: 1000). As shown in Table 17, the specific activities of CLPC (molecular weight: 4000) and AGPC (using a mixture of PEG having a molecular weight of 4000 and a molecular weight of 1000) are 0.6 mU and 0.8 mU, respectively (see FIG. 19). An effect that improved oxidation activity was observed in the case of coating the PC with a low molecular weight coating having a molecular weight of 1000. The values in FIG. 19 were calculated according to the formulas indicated below.

Calculation Formulas—initial velocity (IV, mM/h), activity (AC, mmol/(4 ml·min)), specific activity (SA, units (mmol/(4 mL·min):

Δketone (mM)÷time (h),

AC=IV (mM/h)×0.004 (4 mL/L)×1000 (M/mM)÷60 (min/h)

SA=AC (mol/(4 ml·min))÷$CLPX_a$ (or AGPX) (mg).

In the present invention, AGPC refers to that obtained by adding mixed PEG having molecular weights of 1000 and 4000 (ratio: 1/2) at a concentration level of 0.5% to 1% PEG (v/v) with respect to the amount of buffer during the PC activation treatment of the second step in FIG. 1 (roughly 5 equivalents of 0.5 mM glycine NaOH buffer (pH 9.0 to pH 10.0) with respect to concentrated precipitate) and allowing to stand undisturbed followed by centrifugal separation and crushing by vacuum freeze-drying (FD) the resulting activated precipitate.

In the present invention, in the case the polymer compound is a mixture of different molecular weights, there are cases in which a description thereof may be omitted. For example, in the case of a description in the manner of PEG: molecular weight 1000/4000=2/1, this indicates a mixture of polyethylene glycols having molecular weights of 4000 and 1000, and that the mixing ratio thereof is 2:1.

Figure 19:
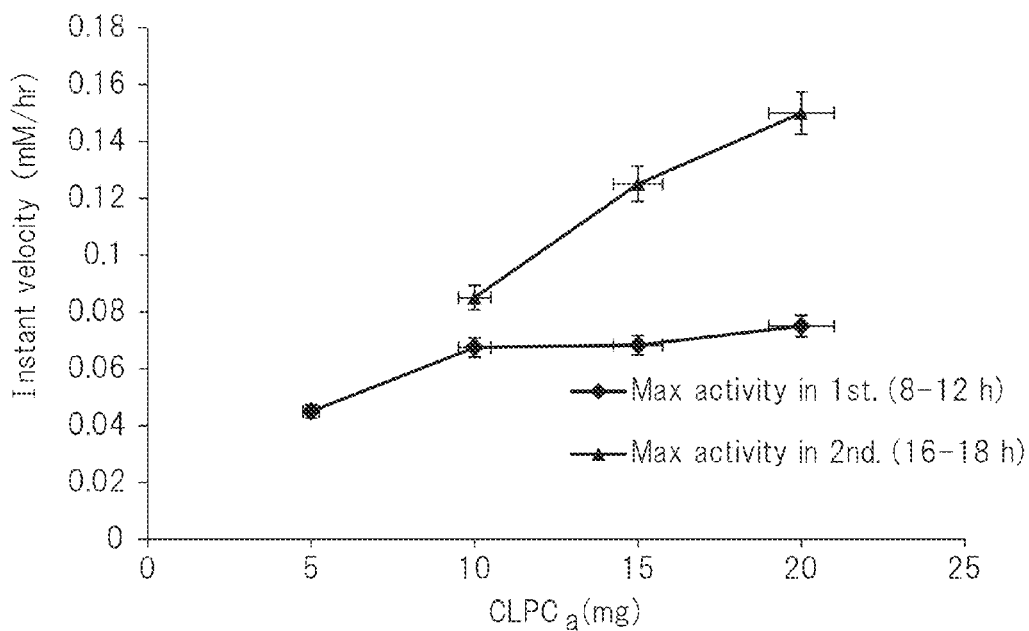
FIGS. 19(a) and 19(b) indicate graphs wherein specific activity was determined for CLPC (PEG-MW: 4000) and AGPC (PEG-MW: 4000/1000=1/2).
Figure 19:
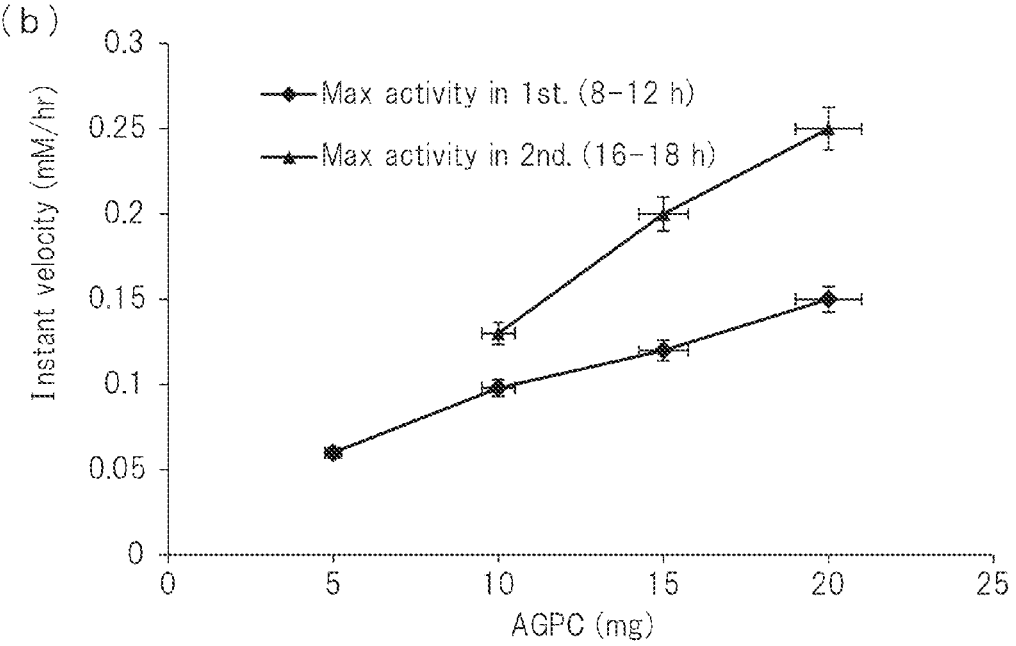

Although detailed data is shown in Example 22 and FIG. 19, it is important to note that, as a result of changing the molecular weight of PEG from 4000 to 1000, the S-isomer is selectively inverted from an R-isomer selective oxidation reaction on a substrate such as Rac-1. Moreover, it is also important to note that, after the S-isomer has been (selectively) oxidized and consumed, the R-isomer is subsequently oxidized and entirely oxidized to ketone. Oxidation of the S-isomer is nearly always observed in an oxidation reaction involving PEG-PC or CLPC that uses PEG having a molecular weight of 4000.

Namely, in the present invention, an R-isomer-selective oxidation reaction (or S-isomer-selective oxidation reaction) can be selected by using as a borderline an environment in which PEG having a molecular weight of 4000 (or including that having a molecular weight of 1000) is present at an aqueous solution concentration level of 0.5% to 1% PEG (v/v) with respect to the amount of buffer during PC activation treatment in the second step of FIG. 1 (consisting of redissolving the concentrated precipitate with roughly 5 equivalents of 0.5 mM glycine NaOH buffer (pH 9.0 to pH 10.0)), thereby enabling a so-called "dynamic" selective oxidation reaction.

Moreover, in the present invention, after the R-isomer or S-isomer is oxidized and consumed by a selective oxidation reaction, since the other enantiomer (S-isomer or R-isomer) can subsequently be obtained, both enantiomers can be selectively obtained both efficiently and easily by a so-called one-pot reaction.

In the present invention, a high molecular weight polymer may be preferably used for the polymer compound in order to carry out an R-isomer-selective oxidation reaction. The molecular weight thereof may preferably be 4000 or more. Although there are no particular limitations on the upper limit of molecular weight, in the case of PEG, that having a molecular weight of 50000 or less may be indicated in order to distinguish from polyethylene oxide.

In the present invention, a polymer compound that includes a low molecular weight polymer (such as a mixture of a high molecular weight polymer and a low molecular weight polymer) may be preferably used as a polymer compound in order to carry out an S-isomer-selective oxidation reaction. The molecular weight thereof may preferably be 1000 or less. This is because, if the molecular weight is excessively large, there is the risk of the occurrence of the above-mentioned R-isomer-selective oxidation reaction. Although there are no particular limitations on the lower limit of molecular weight, in the case of PEG, polymers having a low molecular weight are commercially available that have a molecular weight of about 200. For example, a mixture of PEG having a molecular weight of 200 and PEG having a molecular weight of 20000 can be purchased from Toho Chemical Industry Co., Ltd.

Examples of a mixture of high molecular weight polymer and low molecular weight polymer include a mixture of polyethylene glycols having a molecular weight of 4000 and a molecular weight of 1000. The above-mentioned mixture may preferably contain the low molecular weight polymer at a ratio of 1/3 or more. This is because, in the case the amount contained is less than a ratio of 1/3, there is the risk of the occurrence of the above-mentioned R-isomer-selective oxidation reaction.

EXAMPLES

Although the following provides a detailed explanation of the present invention based on examples thereof, these examples are provided for the purpose of explanation, and should be understood to not limit the present invention.

Furthermore, in each of the examples, the chemically-modified protein complex (CLPC) was obtained according to the process described in Example 1 of Patent Document 3.

Example 1

3000 mL of distilled water were added to 300 g of pea protein (trade name: "Green Pea Protein PP-CS", Organo Foodtech Corp.) followed by further adding 3000 mL of 3% aqueous sodium alginate solution and stirring until homogeneous. The resulting crude protein-sodium alginate mixture was dropped into a 4% aqueous calcium chloride solution using a separatory funnel while stirring to produce gel beads.

Next, after discarding the solution portion, the above-mentioned gel beads were recovered and oxidized in air by allowing to stand undisturbed in air for 5 hours.

4000 mL of distilled water were added to the air-oxidized gel beads followed by shaking for 48 hours at 40° C. using a constant-temperature shaking incubator and eluting the PC in the gel beads to obtain a PC suspension.

The above-mentioned PC suspension was then centrifuged for 10 minutes at 10,000 rpm using a centrifuge (Himac CR20G, Hitachi Koki Co., Ltd.) to obtain a PC precipitate (80 g to 120 g).

After uniformly mixing 100 g of this PC precipitate with roughly 5 equivalents of 0.5 mM aqueous glycine sodium hydroxide solution (pH 9.0 to pH 10.0, 500 mL), 1.0% (v/v) of PEG (MW: 4000) and 2.0% (v/v) of glutaraldehyde (GA) were added and stirred well to obtain a PC suspension in the presence of a polymer compound.

After freeze-drying the resulting polymer compound and PC suspension at −50° C. using a vacuum freeze-dryer (RLEII203, Nissei Ltd.), a vacuum was drawn in the system followed by raising the temperature to 50° C. and causing the moisture to sublimate. Subsequently, the desiccated polymer compound-coated PC was made into a powder by crushing with a ball mill to obtain the HPC-PC of the present invention.

Example 2

(Constituent Element Analysis of Protein Complex (CLPC, PEG-PC) of the Present Invention)

FIG. 3 indicates the results of analyzing (i) pea protein (PP), (ii) CLPC, and (iii) PEG-PC for inorganic elements (Na, Mg, P, S, Ca, Fe, Zn, Mn and Cu) using an ICP emission analyzer (ICPS-7500, Shimadzu Corp.) and for constituent elements (C, H, N and S) using an elemental analyzer (PE2400 II, PerkinElmer Japan Co., Ltd.) for the purpose of determining the residual amounts of raw materials in the PC eluted from the air-oxidized biological material-encapsulated gel. In addition, oxygen content was derived based on molar ratio by system (ICP-90, Nippon Dionex K.K.).

Figure 2:
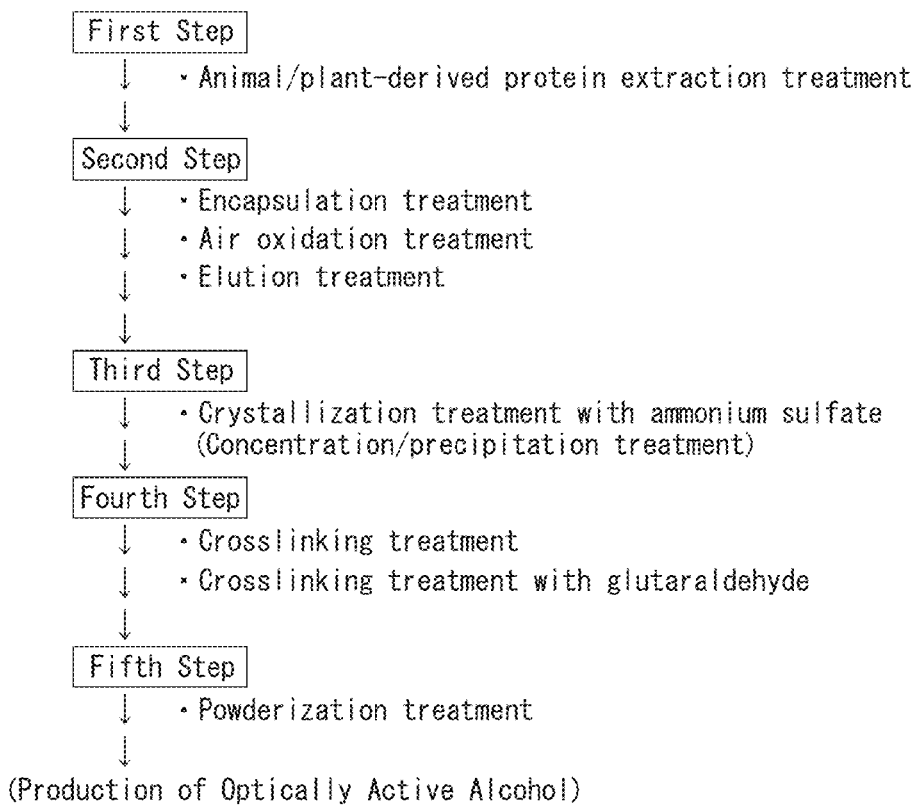
FIG. 2 is a conceptual diagram representing one aspect of a process for producing a chemically-modified protein complex (to be referred to as CL-PC).

As summarized in Table 1, inorganic elements were concentrated roughly nine times more in PEG-PC in comparison with CLPC. With respect to constituent elements, CLPC was determined to have remarkably high contents of sulfur (S) and nitrogen (N), and 10% or more of the raw material ammonium sulfate (($NH_4)_2SO_4$) remained. PEG-PC was presumed to be able to preferably concentrate iron-binding protein from green pea protein by roughly a factor of 4. On the basis of the above, the PEG-PC concentration process shown in FIG. 1 was judged to be superior to the CLPC concentration process shown in FIG. 2 in terms of preventing impurities from remaining in advance. Although the CLPC structure, in which 2.6% $Ca^{2+}$ surrounding the PC is further covered with 10% or more of ammonium sulfate, significantly decreases the ability of a substrate to pass along the surface of the PC and reach the active center thereof, it is also thought to realize a long half-life.

Example 3

(FT-IR Analysis of Protein Complex (CLPC, PEG-PC) of the Present Invention)

FIG. 4 indicates the results of investigating (i) pea protein, (ii) polyethylene glycol (PEG), (iii) PEG-PC (not using ammonium sulfate: Sanyo Catalyst 1), (iv) PEG-PC (using ammonium sulfate: Sanyo Catalyst 2) and (v) sodium alginate by FT-IR (Portable ATR System (A2 Technologies, ML Version), ATR method (ST Japan Inc.) for the purpose of examining residual sodium alginate of the HPC-PC and CLPC. PEG-PC (using ammonium sulfate: Sanyo Catalyst 2) refers to that obtained by centrifuging the result of adding 30% ammonium sulfate to the PC suspension obtained in the first step followed by freeze-drying the resulting precipitate. Furthermore, Table 1 indicates a comparison of the residual ratios of raw materials between CLPC and PEG-PC derived on the basis of data obtained from Example 2 (FIG. 3) and Example 3 (FIG. 4).

TABLE 1

| Sample | From Results of FIG. 3 | | Raw Material Residual Ratios from FIG. 4 | |
|---|---|---|---|---|
| | Inorganic elements | Element concentration | Organic elements | Source Raw Materials |
| CLPC | 0.47% (Fe: 59 ppm) | S: 10.9%, N: 16.09% | 88.92% | Ammonium sulfate, alginic acid, PP → S, N and O are derived from raw materials |
| PEG-PC | 3.75% (Fe: 215 ppm) | Ca: 2.6% | 73.74% | PEG and green pea (PP) → S and N are derived from PP |

Based on FIG. 4(a), (iii) PEG-PC (Sanyo Catalyst 1) has at least one peak in the region of 1085±50 cm-1 in the same manner as PEG-PC (using ammonium sulfate: Sanyo Catalyst 2) and CLPC (Sanyo Catalyst 8_64_2011), and the presence of sulfur oxide (S=O) differing from ammonium sulfate, such as the formation of sulfur oxide (S=O and/or S—O) by cysteine-cysteine disulfide bonds due to air oxidation of the raw material PP, and/or the reduction of iron molecules within the hemophore (iron-capturing protein) causing the PC per se to change to water solubility, are thought to be the cause thereof. Based on Table 1, the reason for the iron content of PEG-PC being concentrated to about 4 times that of CLPC is thought to be that the ammonium sulfate and sodium alginate remaining at 10% or more in the CLPC prevents the concentration thereof.

Moreover, a compound search was carried out on the PEG-PC spectrum using screening software installed in an ATR system. A search was made of the PEG-PC (Sanyo Catalyst 1) using compound search software (MicroLab with Ichem/Aldrich ATR Standard Library (Vols. 1 and 2)), and the results thereof are shown in Table 2.

TABLE 2

| Evaluation Score | Compounds Found in Library |
|---|---|
| 93.75% | Protamine sulfate (CAS No. 53597-250-4) |
| 93.63% | Cis-diacetatotetraamine cobalt (III) perchlorate (CAS No. 53597-25-4) |

Based on Table 2, PEG-PC was judged to be a compound that is 93.75% similar to protamine sulfate. Protamine is a strongly cationic protein obtained from the mature testes of salmon and other species of fish. Thus, PC was indicated to be a cationic protein in the same manner as iron-binding proteins. In addition, protamine sulfate is a pharmaceutical that is used as a heparin antagonist that has blood anticoagulation action, and the same can be expected of the pharmacological effects of PEG-PC as well.

Example 4

(Biochemical Properties of Pea Protein-Calcium Alginate Gel Beads of Second Step)

In the first step, distilled water was added to pea protein-calcium alginate gel followed by stirring in a jar fermenter in a sealed container and monitoring changes in dissolved oxygen (DO) concentration and pH over time. The supply of oxygen was started 24 hours later.

According to the results of FIG. 8, dissolved oxygen (DO) concentration in a jar fermenter in a sealed container in which the supply of oxygen had been interrupted fell nearly to zero in a few hours and pH shifted towards the acidic side. When the supply of oxygen was started, the solution gradually became turbid while at the same time, DO stabilized in the vicinity of 0.6 mg/L and pH began to shift towards the alkaline side. The state of elution of cationic protein (protein complex) at the pH at which oxygen was supplied was monitored.

Based on Table 1 (iron concentration four times higher) and Table 3 (presence of cationic protein), protein (enzyme) retaining iron electron transfer involved in a redox reaction was suggested to be involved. Thus, the protein complex (PC) can be clearly determined to be present by dependence on coenzyme ([Chemical Formula 5] or confirming the function of the oxygen/iron system ([Chemical Formula 6]).

Example 5

(Determination of Active Fraction of PC Suspension)

Asymmetric oxidation reactions were investigated in a centrifuge tube (uncapped) having a diameter of 18 mm while stirring at 700 rpm and 40° C. for the (i) PC suspension (3 ml) and centrifuged fraction thereof (10000 rpm, 10 min), (ii) precipitate (100 mg+3 mL of distilled water) and (iii) supernatant (3 mL) obtained in the first step, as well as (iv) CMC-PC (carboxymethyl cellulose-coated PC, 15 mg+3 mL of distilled water) and (v) CLPC (15 mg+3 mL of distilled water). At that time, a substrate solution of Rac-1 in DMSO (20000 ppm, 30 µL) was added to substrate concentration in an aqueous solution of 0.8 mM. Furthermore, CMC-PC was obtained by coating the precipitate (1 g) with carboxymethyl cellulose (30 mg to 40 mg). CLPC was in the form of a powder obtained by adding 30% ammonium sulfate to the PC suspension followed by chemically modifying the precipitate with glutaraldehyde (0.25% (v/v)) and subjecting to FD treatment.

Figure 9:
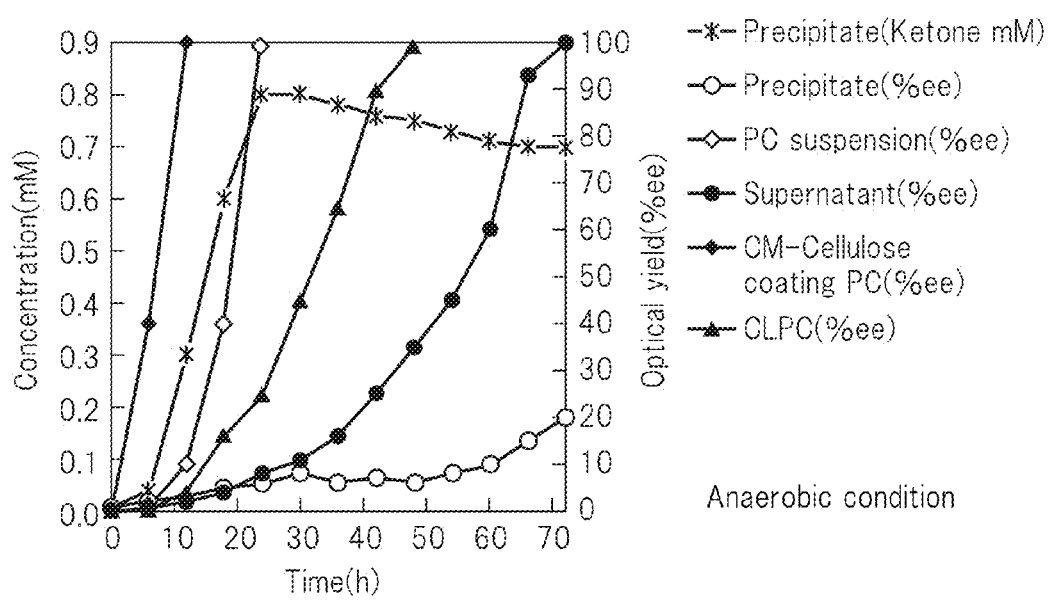
FIG. 9 is a graph indicating an example of differences in the activity levels of fractions obtained following centrifugal separation of a protein complex suspension (PC suspension) (supernatant and precipitate), CLPC and HPC-PC.

According to the results shown in FIG. 9, activity level was obtained with CMC-PC (carboxymethyl cellulose-coated PC: 13 hours), protein complex suspension (PC suspension: 24 hours), CLPC: 48 hours, and supernatant: 72 hours. Furthermore, in a reaction of uncoated precipitate, stereoselectivity was impaired and both enantiomers were completely oxidized. On the basis of the above, although CMC-PC demonstrates the highest level of activity, PC not coated with a polymer compound was unable to maintain stereoselectivity. Moreover, in the PC asymmetric oxidation reaction, the reaction proceeded as is without adding coenzyme (NAD(P) and FAD) and with the cap of the reaction test tube left off.

Example 6

(Study of Air Oxidation Time of Pea Protein-Calcium Alginate Gel)

In the first step of Example 1, (a) pea protein was encapsulated with calcium alginate gel and oxidized in air for 5 hours followed by shake culturing in water (48 hours, 40° C.), precipitating and centrifuging the resulting protein complex suspension with different concentrations of ammonium sulfate (30%, 30%-50%, 50%-70% and >70% (w/v)) and freeze-drying the precipitate to investigate the activity level thereof. Moreover, (b) the ammonium sulfate precipitate (30% (w/v)) was centrifuged after changing the air oxidation time (0, 0.5, 1.0, 3.0, 5.0 and 7.0 hours) followed by freeze-drying the resulting precipitate to a powder to investigate the activity level thereof.

Figure 10:
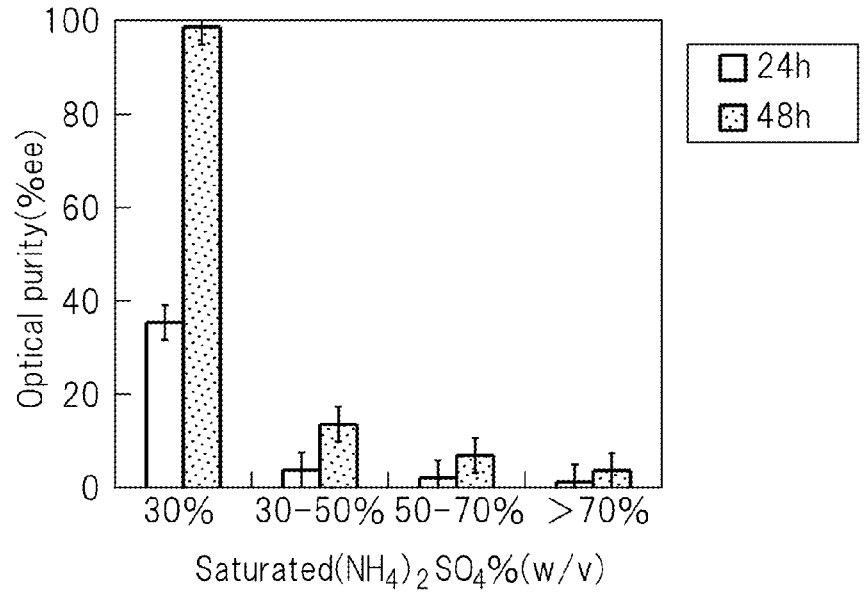
FIGS. 10(a) and 10(b) are graphs indicating (a) an example of differences in 24-hour activity and 48-hour activity of CLPC of precipitated fractions at each ammonium sulfate concentration of a PC suspension obtain in Step 1, and (b) a graph indicating an example of the relationship of CLPC yield and activity level affecting air oxidation time of a pea protein-encapsulated gel.
Figure 10:
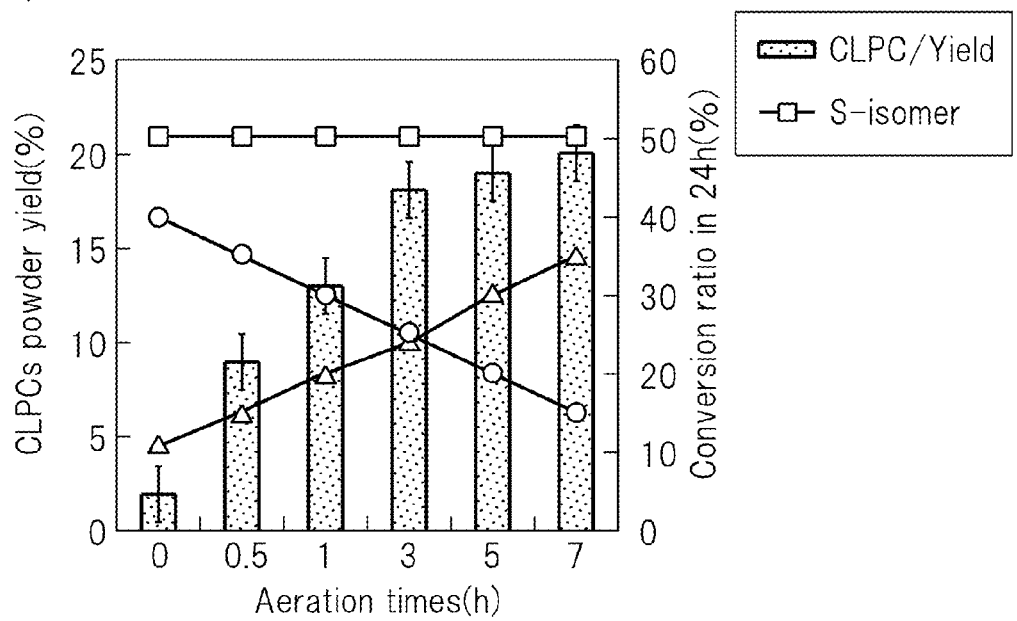

According to the results shown in FIG. 10(a), the protein complex was determined to be able to be preferably recovered from the resulting protein complex suspension at an ammonium sulfate concentration of 30%. Moreover, according to the results shown in FIG. 10(b), air oxidation time is carried out for 3 hours or more and may be preferably carried out for 5 hours or more, and air oxidation time had an effect on PC yield and activity level. A short air oxidation time resulted in a dramatic decrease in PC yield, while conversely, an air oxidation time of 5 hours resulted in a 20% improvement in yield while activity tended to decrease slightly.

Example 7

(Determination of Fraction having Strong Activity in Protein Complex of the Present Invention)

FIG. 5(a) indicates the HPLC spectra demonstrated by three samples appearing at 280 nm at which a supernatant fraction obtained by centrifugal separation (supernatant: 72 hour activity) was fractionated by gel filtration chromatography. FIG. 5(b) indicates the results for the HPLC spectra observed for sample numbers 33 to 36. Moreover, the photograph depicts sample numbers 31 to 39 at 48 hours after the reaction.

The upper chromatogram of FIG. 5(a) indicates a supernatant sample obtained by centrifuging (10,000 rpm, 10 minutes) the PC suspension obtained in the first step of FIG. 1, the middle chromatogram indicates a sample of a 5% aqueous solution of pea protein (PP) powder, and the lower chromatogram indicates a molecular marker solution containing the following proteins:

a: ferritin (440 kDa), b: aldolase (158 kDa), c: conalbumin (75 kDa), d: ovalbumin (44 kDa), e: carbonic anhydrase (29 kDa), f: ribonuclease A (13.7 kDa), and g: aprotinin (6.5 kDa).

Each of the sample solutions were applied to a gel filtration chromatograph following ultrafiltration. The AKTA Explorer manufactured by GE Healthcare Japan Corp. was used for the apparatus, and the HiLoad 16/60 Superdex 200 pg column was used for the column. The column temperature was 4° C. and the flow rate was set to 0.5 mL/min. A developing solution obtained by adding to 50 mM Tris-HCl buffer (pH 8.0) to a salt concentration of 150 mM was used for the developing solution.

FIG. 5(b) shows the results of HPLC analysis when a substrate in the form of a DMSO solution of Rac-2 (20,000 rpm, 30 µL) was added to each of 60 fractions fractionated in 3 mL aliquots followed by reacting each for 48 hours while stirring at 700 rpm using test tubes having a diameter of 18 mm at room temperature of 40° C. and analyzing by HPLC at that time.

Figure 5:
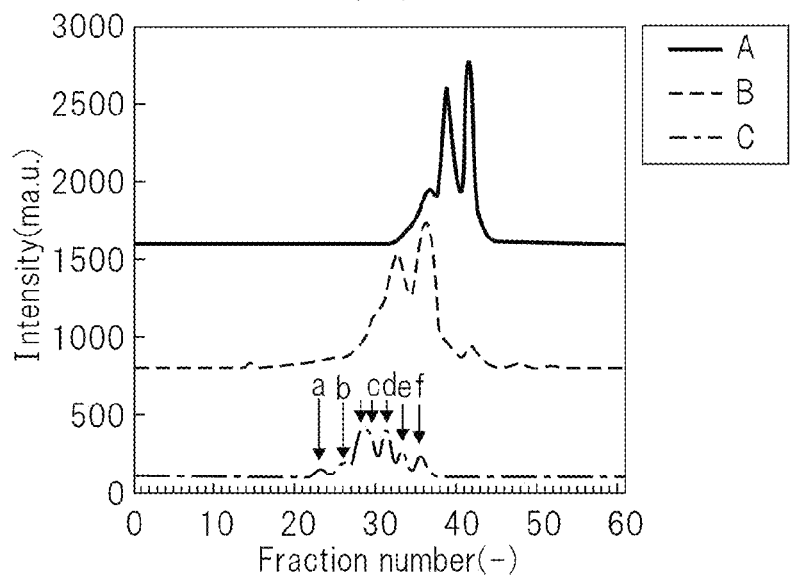
FIGS. 5(a) and 5(b) are examples of graphs and photograph of (a) gel filtration chromatography fractions and (b) HPLC results indicating the asymmetric oxidation intensity of each fraction of one aspect of a supernatant fraction obtained by centrifugally separating an aqueous solution of a protein complex (PC) obtained in a Step 1.
Figure 5:
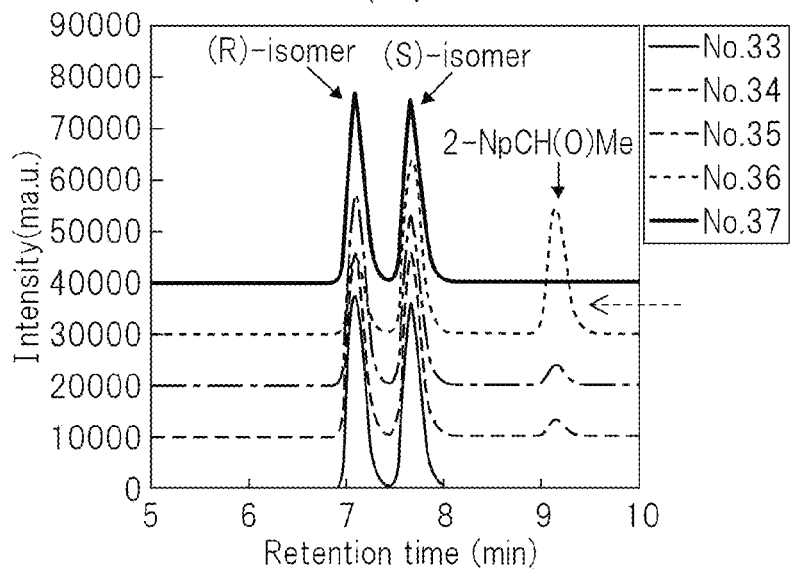
Figure 5:
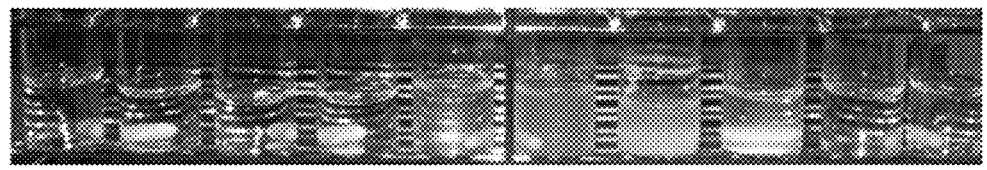

The photograph shown in FIG. 5(b) indicates the results for fraction nos. 30 to 39. According to FIG. 5, the 36th fraction (fraction 36) was confirmed to have the most potent asymmetric oxidation activity.

Example 8

(SDS-PAGE on Fraction Having Potent Activity)

Molecular weight was determined for 10 µl aliquots of each of the following samples A to F and for a molecular weight marker using a precast gel (SDS-PAGE mini) manufactured by Tefco Inc. CBB stain was used to stain the samples. Furthermore, the samples were centrifuged at 10,000 rpm for 10 minutes using the Himac CR20G manufactured by Hitachi Koki Co., Ltd.

A) Protein complex suspension obtained in the second step of Example 1

B) Aqueous solution obtained by centrifuging 10 mL of Sample A followed by redissolving the resulting precipitate in 10 mL of water C) Supernatant obtained following centrifugation of 10 mL of Sample A D) Aqueous solution obtained by adding 30% ammonium sulfate to Sample C and redissolving the resulting precipitate in 10 mL of water E) Aqueous solution obtained by adding 30% ammonium sulfate to Sample A followed by centrifuging and redissolving the resulting precipitate in 10 mL of water F) Fraction 36 obtained in Example 4

The results are shown in FIG. 6. According to FIG. 6, the above-mentioned Fraction 36 was confirmed as a single band (band 7) in the vicinity of 20 kDa.

Example 9

(Protein Identification of Fraction having Potent Activity)

The SDS band of Fraction 36 obtained in Example 5 (band 7 of Sample F shown in FIG. 6) was cut out and the amino acid sequence thereof was analyzed with a protein sequencer (PPSQ-21A, Shimadzu Corp.). The results are shown in Table 3.

TABLE 3

Cycle No. for fraction 36 (band 7)
N-terminal amino-acid sequence identified (33 residues)
 1. $X^a$ S $X^a$ S I S Y S T $X^b$   Y A T N T V A Q Y L   $X^a$ D W $X^b$ A Y F G D L   N H R E Cycle No. for YP 262445.1$^c$
Protein sequence based on a BLAST query sequence analysis
 1. M S I S I S Y S A T   Y G G N T V A G Y L   T D W S A Y F G D V   N [H] R P G E V V D G

T N T G G F N P G P

50. F D G T Q Y A I K S   T A S D A A F V A D   G N L H [Y] T L F S N   P S H T [L] W G S V D

T I S L G D T L A G

100. G S G S N Y N L V S   Q E V S F T N L G L   N S L K E E G R A G   E V H K V V Y G L M

S G D S S A L A G E

150. I D A L L K A I D P   S L S V N S T F D D   L A A A G V A H V N   P A A A A A A D V G

L V G V Q D V A Q D

200. W A L A A $X^a$: may be Cys (C) but not detected,
$X^b$: many amino acids were detected.
$^c$YP 262445.1: The accession hit on the query sequence was limited between the query coverage (>93%) and E value (2e-11), a 20.853 Da HasAp gene product [hemophore: *Pseudomonas fluorescens* Pf-5] from plant commensal bacteria, which can inhibit the rhizosphere and produce secondary metabolites that suppress soil-borne plant pathogens.
Red amino acids indicate "hits" between fraction 36 and YP 262455.1$^c$.
Squares incicate the heme-binding site: His-32 (bearing loop), Tyr-75 (axial heme ligand), and His-83 (hydrogen ligand).

Moreover, the amino acid sequence of Table 3 was analyzed using a protein identification database (BLAST). BLAST can be used to identify proteins by entering the amino acid sequence that is desired to be searched into a text box of "protein blast" on the BLAST analysis site of the American National Center for Biotechnology Information (NCBI, http://blast.ncbi.nlm.nih.gov/). Those blast query results yielding query coverage of 93% or more are shown in Table 4.

TABLE 4

| Accession | Region | MW | Length | Query coverage | E value |
|---|---|---|---|---|---|
| YP 262445.1 | HasAp | 20853 | 205 | 93% | 2e−11 |
| 3 ELL A | HasAp | NA* | 185 | 93% | 4e−8 |
| YP 001347105.1 | HasAp | 20717 | 205 | 93% | 5e−8 |
| ZP 01366858.1 | HasAp | 20786 | 205 | 93% | 5e−8 |
| NP 252097.1 | HasAp | 20772 | 205 | 93% | 6e−8 |
| AAT 49927.1 | HasAp | NA* | 206 | 93% | 5e−8 |
| GAA 21312.1 | HasAp | NA* | 219 | 93% | 6e−8 |
| 3 MOL A | HasAp | NA* | 184 | 93% | 7e−06 |

*NA = no BLAST correlation.
The accession hit on the query sequence was limited between the query coverage (>93%) and E value (7e−06). a 20.853 kDa HasAp gene product [*Pseudomonas fluorescens* Pf-5].

According to Table 4, the component of Fraction 36 and the active band obtained by SDS-PAGE was an iron-binding protein, and a correlation was discovered with respect to the effect of differences in asymmetric oxidation activity on iron concentration between the CLPC indicated in Table 1 (Fe: 59 ppm, activity: 48 h) and PEG-PC (Fe: 215 ppm, activity: 13 h). Since the iron-binding site of each amino acid of His-32 (bearing loop), Tyr-75 (axial heme ligand) and His-83 (hydrogen ligand) shown in Table 3 can be confirmed at the molecular level using FIG. 21 cited by Non-Patent Document 19, evidence was obtained indicating that the enzyme of the present invention involved in an asymmetric oxidation reaction is an iron-binding protein of an oxygen-dependent iron electron transfer system (including, for example, PQQ-ADD, cytochrome oxidase, P450 as well as peroxidase, catalase and ABC transporter).

Results indicating protein identification by LCMS-IT-TOF (Shimadzu Corp., mode: nanoESI+, MS range: MS1 (m/z 400-1500), MS2 (m/z 50-1500), data-dependent scan, flow rate: 300 mL/min, flow solvent: A=0.1% formic acid/2% acetonitrile, B=0.1% formic acid/80% acetonitrile, gradient: 5-40% B/0-30 min, 40-100% B/30-40 min, 100% B/40-60 min) and MASCOT analysis for each of the SDS bands of Example 5 (shown in FIG. 6, bands 1 to 6) are shown in Table 4 (band 5 only), while protein identification of the other bands of Table 5 were evaluated according to the PMF method (Biflex III (Bruker Daltonics K.K., mode: positive/reflector, matrix: α-cyano-4-hydroxycinnamic acid (CHCA), target plate, peptide calibration standards: angiotensin II ([M+H]+=1046.542), angiotensin I ([M+H]+=1296.685), substance ([M+H]+=1347.736), bombesin ([M+H]+=1619.823), ACTH1-17 ([M+H]+=2093.087), ACTH18-39 ([M+H]+=2465.199)) and MASCOT analysis.

TABLE 5

| Band | Score | Mascot Hit |
|---|---|---|
| 1 | 77 | Sodium-type flagellar protein MotY precursor |
| 2 | 79 | Unnamed protein product [*Clostridium ljungdahlii* DSM 13528] |
| 3 | 79 | GTP diphosphokinase [*Phascolarctobacter succinatutens* YIT 12067] |

TABLE 5-continued

| Band | Score | Mascot Hit |
|------|-------|------------|
| 4 | 80 | Extracellular ligand-binding receptor [*Desulfovibrio africanus* str. Walvis Bay] |
| 5 | >46 | Oligopeptide ABC transporter substrate-binding protein [*Brevibacillus brevis* NBRC 100599] |
| 6 | 72 | Conserved hypothetical protein [*Wolbachia* endosymbiont of *Drosophila ananassae*] |

The protein relating to the succinic acid-producing bacterium of band 3 in Table 5 exhibited complex II in mitochondria, and the location of the eluted protein complex (PC) was suggested to be a membrane protein such as mitochondria. Since the ATP-binding cassette (ABC) transporter family of band 5 was functions in membrane protein, the protein complex (PC) was presumed to be a membrane protein. On the basis of the above, since the protein complex is easily precipitated and concentrated by centrifugal separation, the protein complex can be presumed to be a large polymer compound, namely a membrane protein that retains a plurality of enzymes, including catalase. Moreover, localization of PQQ-dehydrogenase and cytochrome oxidase (CytcO), which retain an iron electron transfer system, in mitochondria as shown in FIG. 20 can be presumed to be the effect of having effectively precipitated and concentrated a membrane protein derived from these cell organelles.

Although the hemophore indicated in Table 3 (iron-capturing protein: heme acquisition system (HSA) A) has been reported to be present in the ABC transporter of Table 5 (band 5), this hemophore per se or a protein containing the same, namely an iron-binding protein such as PQQ-ADD, cytochrome oxidase, P450, peroxidase, catalase or ABC transporter, has been determined to lie at the core of the present invention (from Non-Patent Documents 17 to 19).

Cytochrome p450 is an iron-binding protein found in all forms of living organisms, several types are produced in each living organism, and acts by selecting respectively different molecules. Normally, bacterial form about 20 types while animals form about 60 types of cytochrome p450. On the other hand, since plants such as green peas are required to produce characteristic pigment or toxin for their protection, plants have been reported to produce several hundred types of cytochrome p450 enzyme (from Non-Patent Document 18). Thus, this means that the hemophore per se, or membrane protein containing the same, lying at the core of the present invention carries out an asymmetric oxidation reaction provided exclusively in plants and can be confirmed here at the molecular level.

Example 10

(Study of Thermal Denaturation and Chemical Modification of CLPC)

CLPC (20 mg) was subjected to thermal denaturation treatment in an autoclave (121° C., 20 min) or subjected to chemical modification treatment with DTT (cleavage of disulfide bond) for the purpose of confirming that PC involved in an asymmetric oxidation reaction is an iron-binding protein (enzyme). As a result, as shown in Table 6, the reaction was tracked for 48 hours after adding substrate in the form of Rac-1 (0.8 mM) and Rac-2 (0.8 mM). The reaction was carried out using 50 mM glycine-NaOH buffer (pH 9.0, 5.0 mL) for the reaction solvent at a DMSO concentration of 2.07%.

TABLE 6

| CLPC treatment | | | | Cosolvent | | Products | |
|---|---|---|---|---|---|---|---|
| No. | pretreatment | Times (h)$^a$ | Substrate (0.8 mM) | (2.07% (v/v)) | Catalyst (20 mg) | Compd | OP/% ee$^b$ |
| 1 | none | 48 | rac-2 | DMSO | CLPC$^c$ | (S)-2 | >99 |
| 2 | none | 48 | rac-1 | DMSO | CLPC | (S)-1 | >99 |
| 3 | Autoclaving at 121° C. (20 min) | 48 | rac-2 | DMSO | CLPC | (S)-2 | 1.3 |
| 4 | 6.0M guanidine-HCl/50 mM DTT | 48 | rac-2 | DMSO | CLPC | (S)-2 | 1.4 |

Based on the results of Table 6, PC lost activity as a result of the thermal denaturation treatment and chemical modification treatment. Thus, there was determined to be a high possibility that the essence of the activity of the protein complex having the ability to catalyst an asymmetric oxidation reaction is a protein that binds iron and retains an iron electron transfer system and the like.

Example 11

(Activity Inhibition Test of Various Additives on CLPC Asymmetric Oxidation Reaction)

Trace amounts of the inhibitors shown in Table 7 were added to an ordinary reaction environment followed by investigating the effects thereof for the purpose of confirming that the main unit of the protein complex is an iron-binding protein. Effects of competitive inhibition by 1 mM metal salt solution, inhibition of metal electron transfer by 1 mM aqueous chelating agent solutions, and as an optional test, the addition of a 1 mM aqueous surfactant solution were confirmed. Inhibitory activity 48 hours after adding the additives shown in Table 7 was investigated in a system containing substrate Rac-2 (0.8 mM) and 50 mM glycine-NaOH buffer/DMSO (2.07% (w/v) (pH 9.0, 5.0 mL).

TABLE 7

| No. | CLPC inactivation addititves | | Times (h) [a] | Substrate (0.8 mM) | Cosolvent (2.07% (v/v)) | Catalyst (20 mg) | Products Compd | OP/% ee[b] |
|---|---|---|---|---|---|---|---|---|
| 1 | Metal- | MgSO$_4$ | 48 | rac-2 | DMSO | CLPC[c] | (S)-2 | 91.2 |
| 2 | salts | CaCl$_2$ | | | | | | 97.7 |
| 3 | (1.0 mM) | FeCl$_3$ | | | | | | 79.6 |
| 4 | | MnCl$_2$ | | | | | | 80.4 |
| 5 | | ZnCl$_2$ | | | | | | 1.7 |
| 6 | | NiCl$_2$ | | | | | | 77.7 |
| 7 | | CuSO$_4$ | | | | | | 86.2 |
| 8 | Chelating | EDTA | 48 | rac-2 | DMSO | CLPC | (S)-2 | 1.3 |
| 9 | agent | EDTA | | | | | | 1.4 |
| 10 | (1.0 mM) | o-phenanthroline | | | | | | 1.4 |
| 11 | Surfactant (0.1% (v/v)) | Tween-20 | 48 | rac-2 | DMSO | CLPC | (S)-2 | 1.5 |

[a] Reaction time.
[b] Optical purity determined by HPLC.
[c] Crosslinked protein complex.

According to Table 7, inhibitory activity was observed for an aqueous 1 mM ZnCl$_2$ metal salt solution, and activity was completely lost due to addition of chelating agent (such as EDTA). On the basis of the above, the PC having activity that catalyzes an asymmetric oxidation reaction of the present invention was determined to be a metalloprotein based on iron electron transfer ([Chemical Formula 6]).

Example 12

(Study of Effects of Coated Amount of Polymer Compound and Continuous Substrate Addition on Activity)

Reaction results are shown 13 hours after (a) coating 15 mg of a powder (coated amount: 4 g, 2 g, 1 g, 500 m, not coated (none) or precipitated alone (non-PEG/FD)) of a centrifuged precipitate (precipitate: 1 g after FD, roughly 5 g when set) with PEG (molecular weight: 4000) or PEG (molecular weight: 1000) in an aqueous medium (3.0 ml) in the second step. Reaction results are shown 13 hours after (b) coating 15 mg of a powder of the precipitate (precipitate, powder weight: 1 g) with CM-cellulose (a: 2 g, 1 g, 500 mg, 200 mg or 100 mg) and coating 15 mg of the powder with α-starch (b: 500 mg, 250 mg, 150 mg, 50 mg or 25 mg) in an aqueous medium (3.0 mL). Moreover, the (c) S-isomer (>95% ee) is shown that was obtained when PEG(4000)-coated PC, PEG(1000)-coated PC, CM-cellulose-coated PC and α-starch-coated PC were ultimately reacted for 30 hours after continuously adding (after 0 hours, after 12 hours and after 20 hours) substrate in the form of Rac-2 (1.2 mM) to aqueous solutions (5.0 mL) containing 15 mg of each PC.

Figure 11:
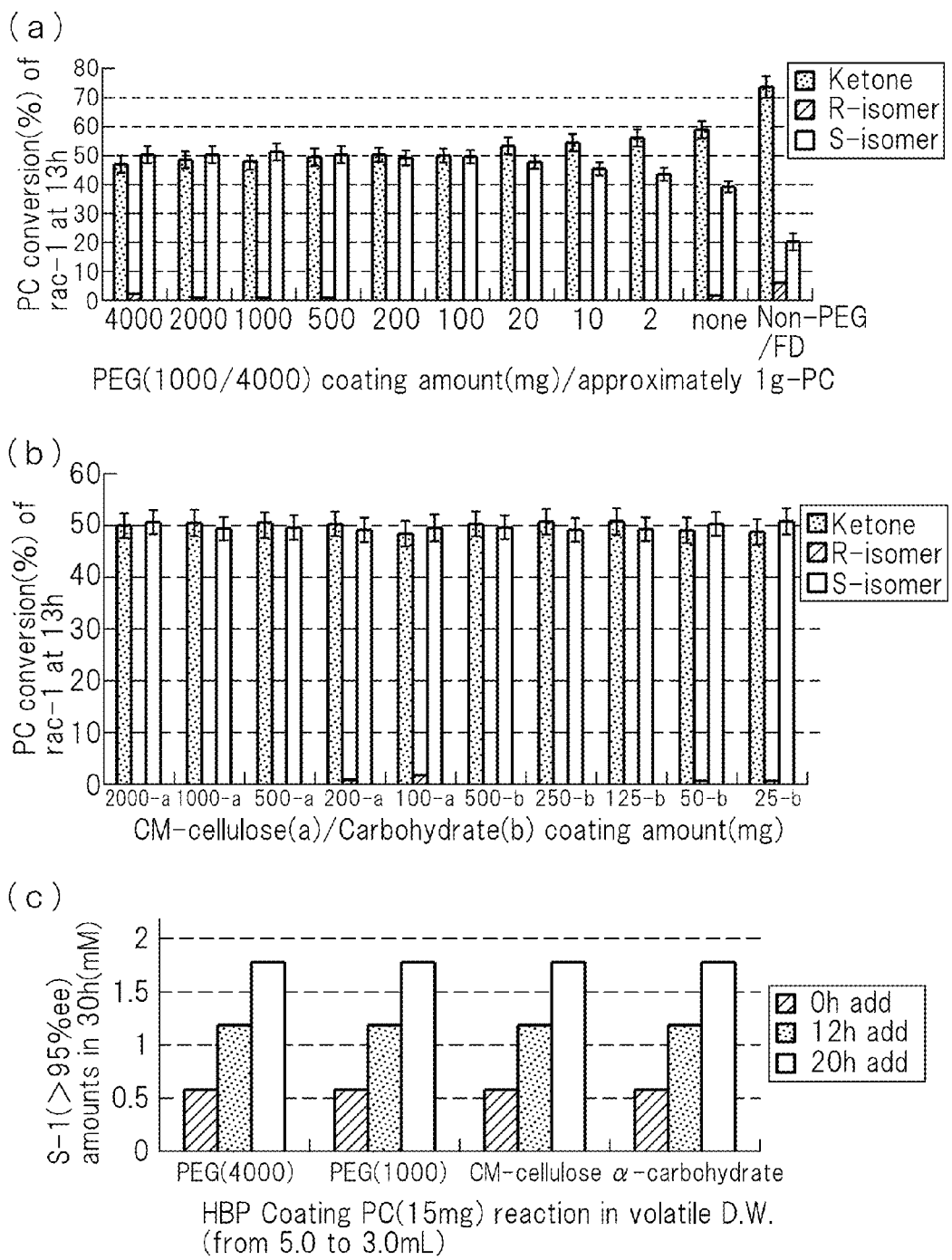

According to the results shown in FIG. 11(a) and FIG. 11(b), the optimal amount of the coated polymer compound was from 200 mg to 500 mg with respect to 5 g of centrifuged precipitate (roughly 1 g after FD), and this was able to be confirmed to act preferably in terms of stereoselectivity of the asymmetric oxidation reaction and activity level. Moreover, 15 mg of polymer compound-coated protein complex required 30 hours in an aqueous solution (5.0 ml), and was shown in FIG. 11(c) to be able to produce 1.8 mM optically active alcohol (roughly 1.0 mg, <98% ee). If the concentration of the coated polymer compound is excessively high, it results in the effect of weakening asymmetric oxidation activity (prolonging reaction time), while conversely, if the concentration is excessively low (or the polymer compound is not added), stereoselectivity was lost and both enantiomers were determined to be oxidized simultaneously. The content of PEG or other polymer compound after FD drying may preferably be about 25%±10% of the content of the protein complex powder, activity weakens if the coated concentration is 50% or more, and conversely, if the coating treatment concentration is 5% or less, a trend was demonstrated in which thermostability (thermal denaturation) due to FD drying treatment and the ability to maintain stereoselectivity (selective collapse) are lost.

Example 13

(Confirmation of Presence of Coenzyme (NAD(P) and FAD) in PC Suspension (3 mL) Reaction System of First Step)

Figure 12:
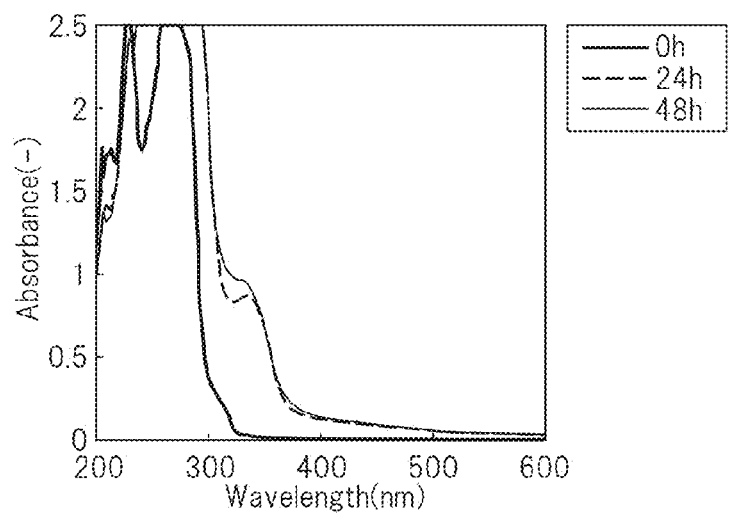
FIGS. 12(a), 12(b) and 12(c) are examples of graphs wherein the presence of coenzyme (NAD(P) and FAD) in a reaction solvent for substrate Rac-1 in a PC suspension obtained in Step 1 was confirmed by UV absorption.
Figure 12:
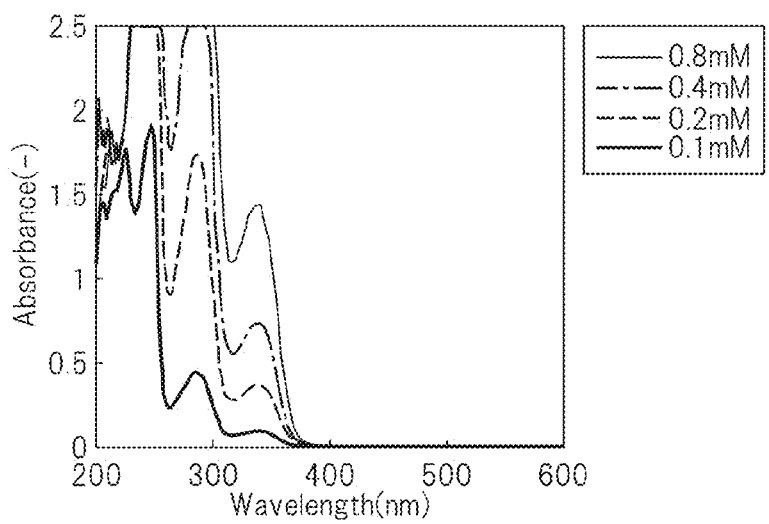
Figure 12:
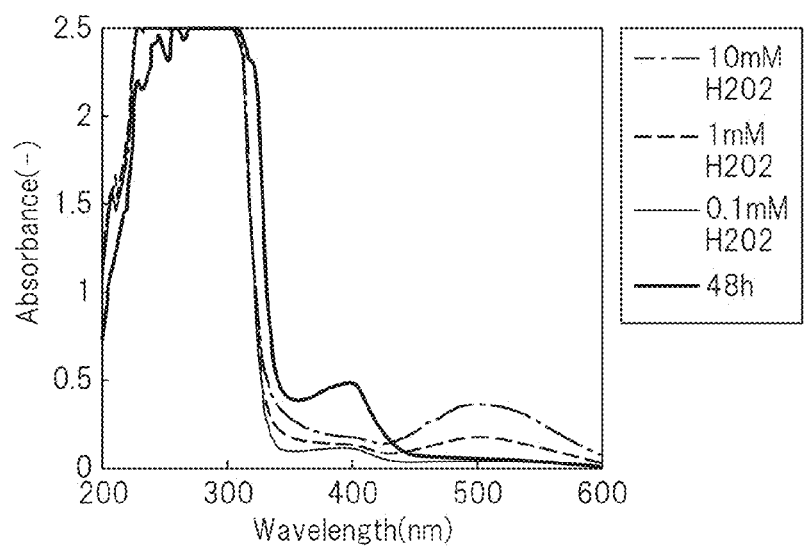

A reaction was carried out using the PC suspension (3 mL) obtained in the first step in an 18 mm diameter centrifuge tube at 40° C. while stirring at 700 rpm. The concentration of the substrate rac-1 (20000 rpm, 30 μL)/DMSO (<0.6% (v/v)) solution was 0.8 mM. FIG. 12(a) shows the results of measuring UV absorbance at 0 hours, 24 hours and 48 hours after the reaction. FIG. 12(b) shows the results of measuring UV absorbance at reaction product (2-acetonaphtone) concentrations of 0.1 mM, 0.2 mM, 0.4 mM and 0.8 mM. FIG. 12(c) shows the results of investigating the change in color and UV absorbance (510 nm) of a solution prepared according to the composition component table of the colorimetric reaction mixture shown in Table 8. Furthermore, the GeneQuant 1300 Personal Spectral Monitor manufactured by GE Healthcare Japan Corp. was used for the spectrophotometer.

TABLE 8

Composition of colorimetric reaction mixture

| Component | Content (μL) |
|---|---|
| supernatant of 48 h reaction mixture | 100 |
| 100 U/mL peroxidase | 100 |
| 2 mM 4-aminoantipyrine | 250 |
| 10 mM phenol | 250 |
| 10 mM Tris-HCl (pH 8.0) | 300 |

Since absorbance observed at 24 hours and 48 hours after the reaction in FIG. 12(a) was confirmed in the vicinity of 340 nm, NAD(P) present in the PC suspension was suggested to be able to completely optically resolve the 0.8 mM substrate in 24 hours. However, since there was no remarkable difference observed in absorbance intensity at 24 hours and 48 hours, and absorbance overlaps with the absorbance at 340 nm demonstrated by the product in the form of 2-acetonaphthone indicated in FIG. 12(b), absorption in the vicinity of 340 nm was determined to be that of the formed ketone and not NAD(P). Moreover, as a result of the colorimetric reaction of FIG. 12(c), since no remarkable changes in color were observed and there were also no remarkable color changes observed at UV absorbance of 510 nM as demonstrated by hydrogen peroxide ($H_2O_2$), the presence of cofactor (NAD(P), FAD) was ruled out.

Example 14

(Study of Buffer Solution (pH) in CLPC Reaction)

The preferable pH was investigated under the reaction conditions of CLPC (20 mg). The reaction conditions consisted of using buffer solutions in the form of 50 mM Tris-HCl (pH: 7.0, 8.0 or 9.0), 50 mM Tris-acetate (pH: 7.0, 8.0 or 9.0), 50 mM phosphate (pH: 6.0, 7.0 or 8.0), 50 mM Pipes-NaOH (pH: 6.1, 7.0 or 7.5) and 50 mM glycine-NaOH (pH 9.0 or 10.0), adding substrate in the form of racemic 1-(2-naphthyl) ethanol (rac-2)/IPA solution (1,000 ppm, 0.8 mL) and respectively relating for 48 hours in 18 mm diameter centrifuge tube at 40° C. while stirring at 700 rpm. The results are shown in Table 9.

TABLE 9

| No. | Reaction solutions Buffers | pH | Times (h)$^a$ | Substrate (0.8 mM) | Cosolvent (4.14% (v/v)) | Catalyst (20 mg) | Products Compd | OP/% ee$^b$ |
|---|---|---|---|---|---|---|---|---|
| 1 | 50 mM | 7.0 | 48 | rac-2 | IPA | CLPC$^c$ | (S)-2 | 7 |
| 2 | Tris-HCl | 8.0 | | | | | (S)-2 | 74 |
| 3 | | 9.0 | | | | | (S)-2 | 84 |
| 4 | 50 mM | 7.0 | 48 | rac-2 | IPA | CLPC | (S)-2 | 1 |
| 5 | Tris-acetate | 8.0 | | | | | (S)-2 | 74 |
| 6 | | 9.0 | | | | | (S)-2 | 92 |
| 7 | 50 mM | 6.0 | 48 | rac-2 | IPA | CLPC | (S)-2 | 1 |
| 8 | Phosphate | 7.0 | | | | | (S)-2 | 6 |
| 9 | | 8.0 | | | | | (S)-2 | 0 |
| 10 | 50 mM | 6.1 | 48 | rac-2 | IPA | CLPC | (S)-2 | 0 |
| 11 | Pipes-NaOH | 7.0 | | | | | (S)-2 | 77 |
| 12 | | 7.5 | | | | | (S)-2 | 75 |
| 13 | 50 mM | 9.0 | 48 | rac-2 | IPA | CLPC | (S)-2 | 98 |
| 14 | Glycine-NaOH | 10.0 | | | | | (S)-2 | 98 |

Based on the results of Table 9, a high level of activity was observed for 50 mM glycine-NaOH (pH 9.0 or 10.0), and 50 mM glycine-NaOH (pH: 9.0) was determined to be suitable for the reaction solvent of CLPC (20 mg).

Example 15

(Study of Cosolvents of CLPC)

After dissolving substrate Rac-1 in cosolvent (DMSO, Log P=−1.49), isopropyl alcohol (IPA, Log P=0.38) or ethanol (Log P=0.07) with CLPC (20 mg), the resulting solution was added to 5.0 mL of 50 mM glycine-NaOH (pH: 9.0) to a prescribed solvent concentration of 2.07% (v/v) and substrate concentration of 0.8 mM, 1.6 mM or 2.0 mM) followed by investigating optical purity at 24 hours and 48 hours after the asymmetric oxidation reaction. Furthermore, the diffusion coefficient (Log P) refers to an indicator of substrate hydrophobicity and transition.

Figure 13:
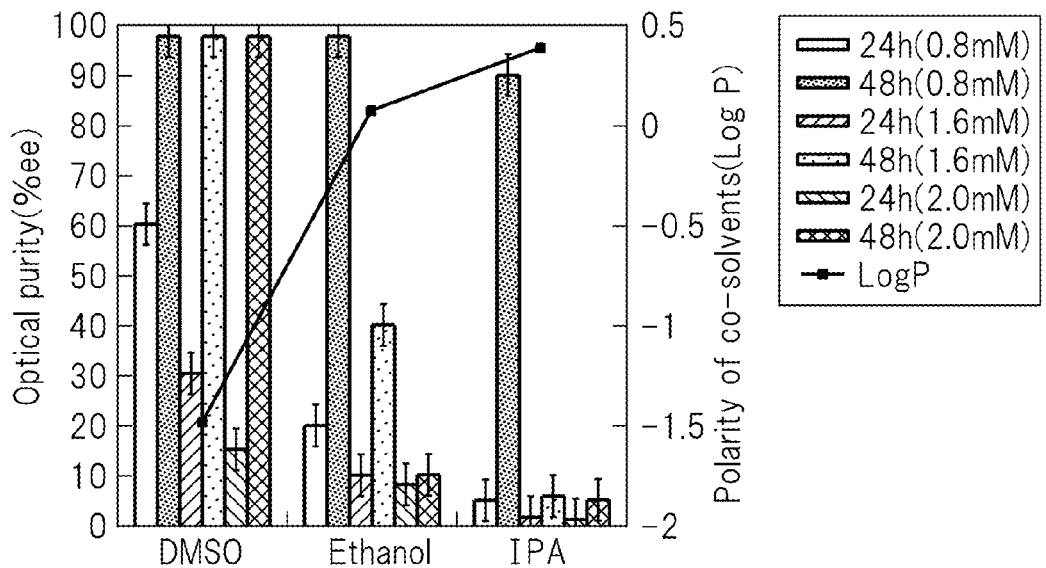
FIG. 13 is an example of a graph indicating the effects of various cosolvents on CLPC activity level.

As shown in FIG. 13, although cosolvent (DMSO, Log P=−1.49) resulted in preferable asymmetric oxidation even at a substrate concentration of 1.6 mM or 2.0 mM, IPA (Log P=0.38) and ethanol (Log P=0.07) required 48 hours for the reaction only at a substrate concentration of 0.8 mM. On the basis thereof, DMSO was indicated to act preferably as cosolvent in a CLPC reaction.

Figure 14:
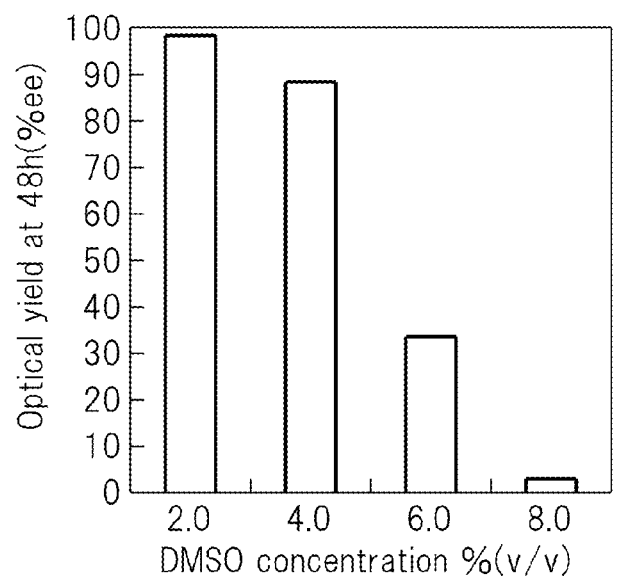
FIG. 14 is an example of a graph indicating the effects of DMSO concentration in a reaction solvent on CLPC activity level.

FIG. 14 summarizes the results of reacting CLPC (20 mg) in a reaction solution consisting of substrate Rac-1 (0.8 mM) in 50 mM glycine-NaOH (pH: 9.0, 5.0 mL) for 48 hours at 40° C. and at a DMSO concentration of 2.0%, 4.0%, 6.0% or 8.0% (v/v). As a result, the asymmetric oxidation reaction proceeded more favorably the lower the concentration of DMSO.

Example 16

(Study of Cosolvent/Buffer Aqueous Medium System in CLPC Reaction and HPC-PC Reaction)

Table 10 indicates the results of reacting using the CLPC-1 (20 mg: using ammonium sulfate), CLPC-2 (20 mg, PC derived from precipitate obtained by centrifugation after adding 30% ammonium sulfate) and HPC-PC (15 mg) used in FIG. 4(a) as enzyme, using Rac-1 or substrate Rac-2 (1.2 mM) as substrate and using DMSO and IPA as cosolvent in a reaction solution consisting of 50 mM glycine-NaOH (pH: 9.0, 4.0 mL) or distilled water (DW, 4.0 ml). Three types of polymer compounds were used for HPC-PC consisting of polyethylene glycol (PEG (molecular weight 1000 or 4000)), carboxymethyl cellulose (CMC) and α-starch (PGS).

HPC-PC was prepared by redissolving a polymer compound (50 g each of PEG, CMC or PGS in 1500 L of water) based on the weight of the PC precipitate (1000 g) followed by subjecting each solution to FD drying to obtain a powder. The reaction results were tracked every 2 to 3 hours. The difference between the preparation of CLPC-1 and CLPC-2 was whether or not centrifuging (10,000 rpm, 10 min) was carried out after the third step in FIG. 2, and both can be subsequently prepared using the same chemical modification and FD drying.

TABLE 10

| PCs | Times (h) [a] | Substrate (12 mM) | Cosolvent [0.6% (v/v)] | Solvent [3.0 mL] | Products Compd | OP/% ee[b] |
|---|---|---|---|---|---|---|
| 1 CLPC-1/20 mg | 48 | rac-1 | IPA[c]/DMSO | DW | (S)-1 | 3.8/58 |
|  | 48 | rac-1 | IPA/DMSO | Buffer[d] | (S)-1 | 79/>99 |
| 2 CLPC-2/20 mg | 48 | rac-2 | IPA[c]/DMSO | DW | (S)-2 | 8.8/13.1 |
|  | 24 | rac-2 | IPA/DMSO | Buffer[d] | (S)-2 | 85/>99 |
| 3 PEG (1000)-PC (15 mg) | 13 | rac-2 | IPA/DMSO | DW | (S)-2 | >99/>99 |
|  | 13 | rac-2 | IPA/DMSO | Buffer | (S)-2 | >99/>99 |
| 4 PEG (4000)-PC (15 mg) | 13 | rac-1 | IPA/DMSO | DW | (S)-1 | >99/>99 |
|  | 13 | rac-1 | IPA/DMSO | Buffer | (S)-1 | >99/>99 |
| 5 CMC-PC (15 mg) | 14 | rac-2 | IPA/DMSO | DW | (S)-2 | >99/>99 |
|  | 13 | rac-2 | IPA/DMSO | Buffer | (S)-2 | >99/>99 |
| 6 PGS-PC (15 mg) | 14 | rac-1 | IPA/DMSO | DW | (S)-1 | >99/>99 |
|  | 14 | rac-1 | IPA/DMSO | Buffer | (S)-1 | >99/>99 |

[a] Reaction time.
[b] Optical purity determined by HPLC.
[c] 2-propanol.
[d] 50 mM Glycine-NaOH (pH 9.0).

According to the results of Table 10, CLPC-2, to which was added a centrifugation step, was confirmed to demonstrate a two-fold improvement in reaction time in comparison with CLPC-1 in a 50 mM glycine-NaOH (pH 9.0)/cosolvent DMSO system. Moreover, in contrast to the reaction not proceeding in an aqueous medium in the case of CLPC, not only did the reaction proceed in an aqueous medium in the case of HPC-PC, but results were obtained in which HPC-PC activity was roughly 4 times more potent in comparison with the activity of CLPC-2 (48 h), exhibiting an activity level of 13 h.

(Summary of Characteristics of Protein Complexes (PC, CLPC and HPC-PC)

Figure 15:
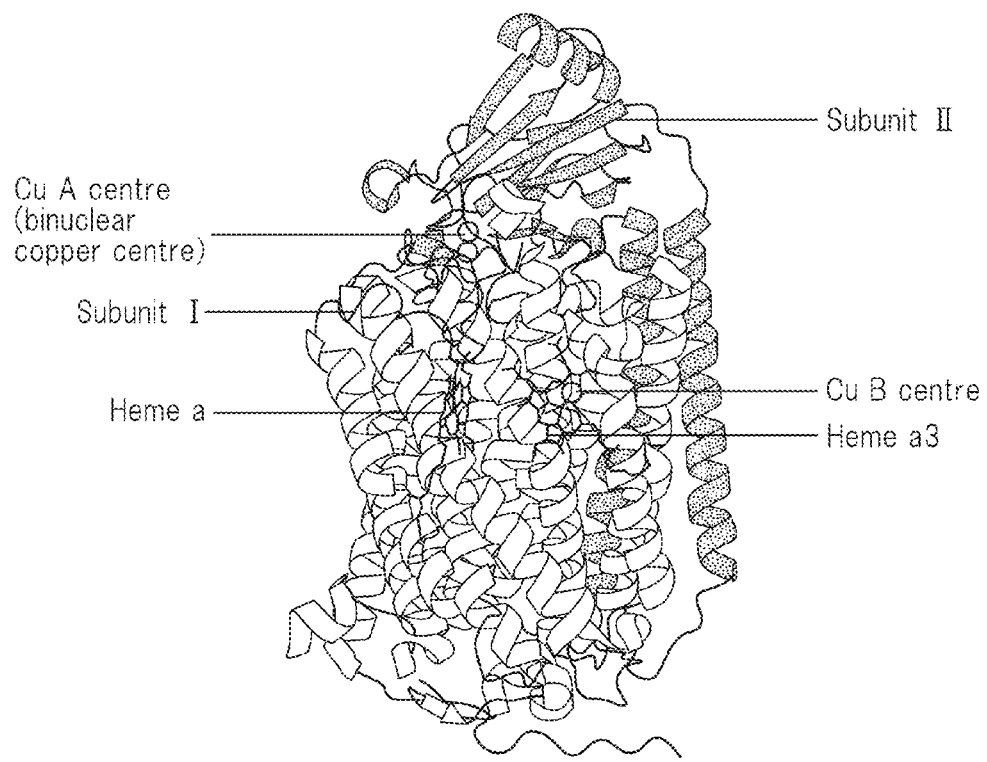
FIG. 15 is an example of a schematic diagram
Figure 15:
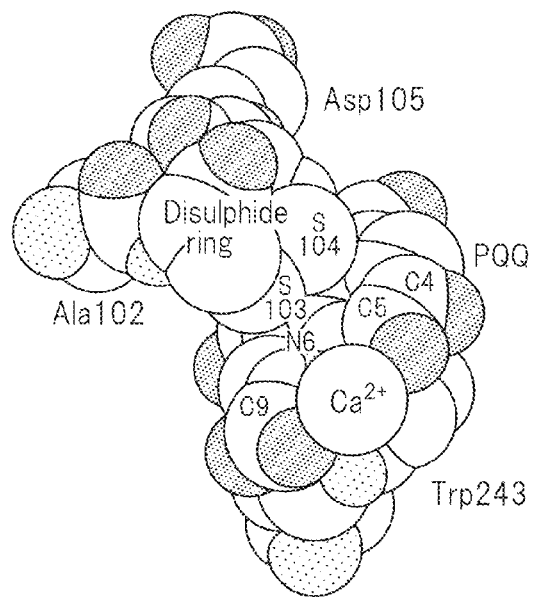
Figure 16:
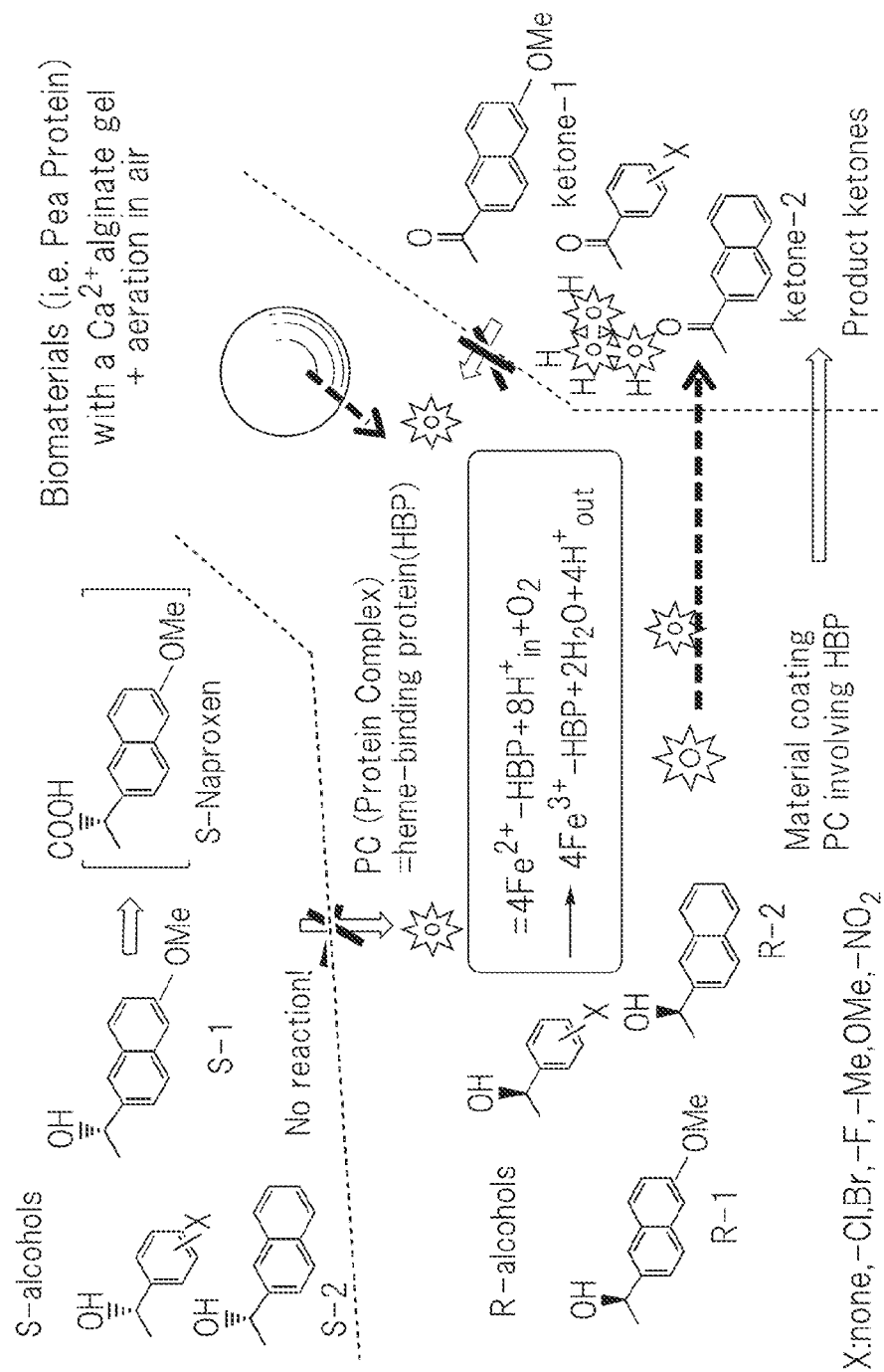
FIG. 16 is an example of a schematic diagram showing a state in which HPC-PC, which was processed from PC eluted from an air-oxidized biological material-encapsulated gel, asymmetrically oxidizes various secondary alcohols.

Characteristics of the three protein complexes are summarized in Table 11 based on suggestions for the preferable concentration process of cationic protein from the inorganic element analyses of FIGS. 3, 4 and 8, reaction properties of the cationic protein and verification of the oxygen-dependent secondary alcohol dehydrogenation reaction from FIGS. 5, 9, 10, 11, 12 and 13 and the discussion that the protein complex is a membrane protein that retains a plurality of enzymes, including catalase, from FIGS. 15 and 16.

In addition, a catalyst test was conducted by placing 15 mg of each sample in an 18 mm diameter centrifuge tube, adding 5% aqueous $H_2O_2$ solution (1 mL) and comparing the heights of the bubbles. The catalase activity of HPC-PC was confirmed to result in a bubble height four times that of CLPC. A correlation was obtained for this result with the iron concentrations of CLPC (59 ppm) and HPC-PC (215 ppm) shown in Table 1. Moreover, a roughly 4-fold difference in asymmetric oxidation activity shown in Table 11 was also observed between CLPC and HPC-PC. Moreover, as shown in Table 10, pH-dependent characteristics attributable to the buffer solution were not observed in the reaction solvent of HPC-PC, and simply carrying out asymmetric oxidation reaction in an aqueous medium was observed to be advantageous.

TABLE 11

| Sample | Activity Level | | Ease of Procedure | | | | Cost |
| | Asymmetric Oxidation | Catalase | Form | Reaction Solvent | Storage | Thermo-stability | Operation/preparation |
|---|---|---|---|---|---|---|---|
| PC | — | — | Precipitate Powder | Water | Freezing | Low | — |
| CLPC | 48 h | * | Powder | Buffer pH adjuster | Room temp. | High | High |
| HPC-PC | 13 h | ***** | Powder | Water | Room temp. | High | Low |

As shown in Tables 1, 10 and 11, the protein complex (PC, CLPC, HPC-PC) was demonstrated to be a membrane protein retaining a plurality of iron-binding proteins (enzymes), including catalase, and was demonstrated to be easily produced by easily going through steps consisting of extraction from a biological raw material, concentration, combining with polymer compound and FD dehydration drying. Among these, the HPC-PC of the present invention was indicated to have especially superior cost performance as well as superior ease of the procedure in the preparation process thereof.

Example 17

(Study of Separate Use of Both Enantiomers Protein Complex (PC) Suspensions Derived from Different Biological Materials)

A study of substrate specificity was carried out between substrates consisting of para-position-substituted Rac-1-phenylethanol and Rac-2 using different biological materials in the second step consisting of protein complexes derived from wakame seaweed (WS), carrot (C), pumpkin (P) (Table 12) and ovalbumin (IOA) (Table 13). The reactions were carried out under reaction conditions using the system for investigating asymmetric oxidation reaction of (i) of Example 5 consisting of placing the PC suspension (3 mL) in an 18 mm diameter centrifuged tube (uncapped) at 40° C. and stirring at 700 rpm, and the substrate Rac-2/DMSO solution (20000 ppm, 30 μL) was added to obtain an aqueous solution having a substrate concentration of 0.8 mM. The results are summarized in Tables 12 and 13. An introduction is provided regarding other different biological materials in Patent Document 1, while an introduction regarding ovalbumin (IOA) is provided in Patent Document 2.

TABLE 12

| Substrate | | Reaction | Plant | Product | | |
|---|---|---|---|---|---|---|
| | Ar | Time | Origin | Comp. | OP/% ee | CY/% |
| 1p | 4-BrC$_6$H$_4$ | 3 | P | S-1p | >99 | 50 |
| 2p | 4-ClC$_6$H$_4$ | 38 | C | S-2p | >99 | 41 |
| | 4-ClC$_6$H$_4$ | 30 | P | S-2p | >99 | 50 |
| 4p | 4-MeC$_6$H$_4$ | 47 | WS | S-4p | >99 | 21 |
| | 4-MeC$_6$H$_4$ | 50 | P | S-4p | >99 | 50 |
| 5p | 4-MeOC$_6$H$_4$ | 47 | WS | S-5p | >99 | 32 |
| | 4-MeOC$_6$H$_4$ | 21 | P | S-5p | >99 | 25 |
| 6 | 2-naphthyl | 31 | AVI | R-6 | >99 | 50 |

Supplement:
Comp.: compound,
OP/% ee: optical purity,
CY/%: chemical yield

TABLE 13

| Substrate | | Reaction | Plant | Product | | |
|---|---|---|---|---|---|---|
| | Ar | Time | Origin | Comp. | OP/% ee | CY/% |
| 1p | 4-BrC$_6$H$_4$ | 24 | IOA | R-1p | 86.6 | 27 |
| 2p | 4-ClC$_6$H$_4$ | 24 | IOA | R-2p | 96.4 | 26 |
| 5p | 4-MeOC$_6$H$_4$ | 24 | IOA | R-5p | 99.8 | 26 |
| 6 | 2-naphthyl | 24 | IOA | R-6 | 85.8 | 24 |

Supplement:
Comp.: compound,
OP/% ee: optical purity,
CY/%: chemical yield

Based on the results of Table 12, protein complex derived from *Artemisia vulgaris* indica (AVI), wakame seaweed (WS), carrot (C) or pumpkin (P) was suitably eluted from a gel while at the same time, a substrate in the form an R-isomer of para-substituted bromine (Br—/1p), chlorine (Cl—/2p), methyl (Me-/4p) or methoxy (MeO—/5p) was selectively oxidized to obtain S-isomer alcohol at a chemical yield of 50% and optical purity of 99% ee, while in the case of substrate Rac-2, an S-isomer was selectively oxidized to obtain R-isomer alcohol at a chemical yield of 26% and optical purity of 85% ee to 95% ee.

Based on the results of Table 13, the protein complex suspension derived from ovalbumin (IOA) allowed the obtaining of an R-isomer alcohol having an optical yield of 26% and optical purity of 85% ee to 95% ee by racemic S-isomer-selective oxidation of substrates consisting of para-substituted bromine (Br—/1p), chlorine (Cl—/2p), methoxy (MeO—/5p) or Rac-2 (naphthyl/6).

On the basis of the above results, there were clearly determined to be two types of animal/plant-derived protein complex (PC) consisting of one that has the property of being able to stereoselectively asymmetrically oxidize only the racemic S-isomer, and the other type that has the property of being able to stereoselectively asymmetrically oxidize only the racemic R-isomer.

Thus, the HPC-PC of the present is further able to provide both that for a reaction that catalyzes S-isomer-selective asymmetric oxidation and that for a reaction that catalyzes R-isomer-selective asymmetric oxidation.

Example 18

(Measurement Catalase Activity: Measurement by Visual Confirmation of "Bubbling")

When 5% H$_2$O$_2$ (1 mL) was respectively added to 18 mm diameter centrifuge tubes containing PEG-PC (15 mg) and CLPC (15 mg) obtained in the above-mentioned Example 3, the PEG-PG solution bubbled violently in comparison with the CLPC solution and the bulk of 1.0 mL of the solution expanded 1.5 to 3.5 times due to bubble volume. However, roughly 5 minutes later, bubbling settled down to the original 1.0 mL of PEG-PC solution. On the other hand, in the CLPC reaction system, bubbling occurred mildly in the surface layer of the solution resulting in generation of oxygen, after which bubbling settled down 5 minutes later.

In each of the following examples, the intensity of catalase activity was investigated by calculating the residual amount of H$_2$O$_2$ following the reaction and the amount of H$_2$O$_2$ consumed.

Example 19

(Measurement of Catalase Activity: Measurement Using "Pack Test")

Each sample of PC catalyst consisting of 1) PEG-PC (15 mg), 2) CLPC (15 mg) and 3) no addition of catalyst was placed in an 18 mm diameter centrifuge tube followed by the addition of an aqueous solution (1 mL) of 5% hydrogen peroxide (H$_2$O$_2$) and stirring (700 rpm) for 5 minutes at 35° C. The H$_2$O$_2$ concentration of the reaction solution (10 μL) was diluted to $\frac{1}{100000}$ with water followed by using in the hydrogen peroxide "Pack Test" (WAK-H$_2$O$_2$, Kyoritsu Chemical-Check Lab Corp.).

At the same time, measurement was carried out under the same conditions while replacing the 5% hydrogen peroxide solution (1 mL) with pure water (1 mL), and the resulting data was indicated as Blank 1 for the PEG-PC (15 mg)/water (1 mL) sample and as Blank 2 for the CLPC (15 mg)/water (1 mL) sample.

This "Pack Test" refers to a measurement method in which peroxidase and a powder comprising four types of phenols and 4-aminoantipyrine are contained in a pack, the powder is in co-presence with aqueous hydrogen peroxide, and the intensity of the purple color formed (corresponding to the amount of quinoneimine formed) is compared with a standard color chart to derive the concentration of hydrogen peroxide. The range of the aqueous hydrogen peroxide (intensity of purple color) is 0 ppm to 5 ppm.

Results obtained according to the above-mentioned measurement are shown in Table 14.

TABLE 14

| 5% Hydrogen Peroxide Solution | Pack Test |
|---|---|
| Blank | 0.5 (×100,000) ppm: 5% |
| PEG-PC (15 mg) | 0.4 (×100,000) ppm: 4% |
| CLPC (15 mg) | 0.9 (×100,000) ppm: 7% |

* Blank 1 = 2.2% (PEG-PC (15 mg)/water (1 mL): no hydrogen peroxide solution)
* Blank 2 = 4.0% (CLPC (15 mg)/water (1 mL): no hydrogen peroxide solution)

Based on the measurement results obtained with the Pack Test, the measured value when using CLPC (7%) exceeded the value of the blank (5%). This measurement result indicated that it is difficult to use this test to measure catalase activity (in the case of CLPC) since an effect that promotes quinoneimine synthesis is observed due to an oxygen donor such as ammonium sulfate contained in CLPC or sulfur oxide (S—O or S═O) derived from PC based on reasons such as the finding that persulfuric acid ($H_2S_2O_6$) also acts in the manner of hydrogen peroxide in this test. On the other hand, in the case of PEG-PC, since contaminants like those described above are not thought to be present, this type of measurement using "Pack Test" is thought to be useful to a certain degree for qualitative and/or semi-quantitative measurement (such as screening).

Furthermore, the following documents or URL can be referred to as necessary regarding details regarding the above-mentioned "Pack Test" and details regarding measurement systems using peroxidase, phenols and 4-aminoantipyrine.
(1) "Pack Test": http://kyoritsu-lab.co.jp/pack/packtest/manual2/wak_h2o2.pdf
(2) Measurement system: Absorptiometric Determination of Phenolic Compounds in Water using 4-Aminoantipyrine, Hydrogen Peroxide and Peroxidase (reference URL: http://ci.nii.ac.jp/naid/110003642714/)
Hygienic Chemistry 24 (4), 175-181, 1978-08-31, Pharmaceutical Society of Japan Example 20

(Measurement of Catalase Activity: Measurement Using Hydrogen Peroxide Concentration Meter)

The catalyst activity of PC was measured using the PAL-39S Hydrogen Peroxide Concentration Meter manufactured by Atago Co., Ltd., which is able to calculate hydrogen peroxide concentration from the intensity of the refractive index of hydrogen peroxide contained in water. Furthermore, the following URL can be referred to as necessary regarding the details of the hydrogen peroxide concentration meter used here.

http://atago.net/japanese/products_pal/top.html

Catalase activity was measured by adding 5% aqueous hydrogen peroxide (1 mL) to each sample consisting of 1) PEG-PC (15 mg) or 2) CLPC (15 mg) in an 18 mm diameter centrifuge tube followed by stirring (700 rpm) for 5 minutes at 37° C. The reaction solution was centrifuged (3600 rpm, 10 min) and 0.3 mL of the resulting supernatant was dropped onto the surface of the prism of the PAL-39S hydrogen peroxide concentration meter to measure catalyst activity. At the same time, catalase activity was measured under the same conditions while replacing the 5% aqueous hydrogen peroxide (1 mL) with pure water (1 mL), PEG-PC (15 mg)/water (1 mL) was designated as Blank 1, while CLPC (15 mg)/water (1 mL) was designated as Blank 2.

On the basis of the above, the amount of $H_2O_2$ consumed in the case of using PEG-PC and the amount of $H_2O_2$ consumed in the case of using CLPC were calculated in the manner indicated below. The results are shown in Table 14.

Residual amount of $H_2O_2$ after reaction (PEG-PC)=(measured value: 8.0%)–(Blank 1 value: 2.2%)=5.8%

Residual amount of $H_2O_2$ after reaction (CLPC)=(measured value: 10.4%)–(Blank 2 value: 4.0%)=6.4%

Amount of $H_2O_2$ consumed (PEG-PC)=residual amount of $H_2O_2$ in Blank system: 6.8%)–(residual amount of $H_2O_2$ after PEG-PC reaction: 5.8%)=1.0% (14.7% consumed as relative value)

Amount of $H_2O_2$ consumed (CLPC)=residual amount of $H_2O_2$ in Blank system: 6.8%)–(residual amount of $H_2O_2$ after CLPC-PC reaction: 6.4%)=0.4% (5.9% consumed as relative value)

TABLE 15

| 5% Hydrogen Peroxide Solution | PAL-39S Concentration Meter | |
|---|---|---|
| Blank | 6.8% | |
| PEG-PC (15 mg) | 5.8% | 2.2% (Blank 1) |
| CLPC (15 mg) | 6.4% | 4.0% (Blank 2) |

* Blank 1 = 2.2% (PEG-PC (15 mg)/water (1 mL): no hydrogen peroxide solution)
* Blank 2 = 4.0% (CLPC (15 mg)/water (1 mL): no hydrogen peroxide solution)

Based on the results obtained using the PAL-39S hydrogen peroxide concentration meter shown in Table 15, the identity of the bubbles generated in the experiment was oxygen, and involvement of an enzyme having catalase activity that converts hydrogen peroxide to water and oxygen was confirmed. Thus, PEG-PC (15 mg) demonstrated catalase activity that consumes roughly 10,000 ppm of 5% hydrogen peroxide solution while CLPC (15 mg) demonstrated catalase activity that consumes roughly 4000 ppm.

Thus, the activity of each PC catalyst (units) can be calculated in the manner indicated below by calculating the amount of PEG-PC or CLPC that is able to convert 1 μmole of substrate ($H_2O_2$: MW 34) per minute.

6.8% aqueous $H_2O_2$=68 mg/mL $H_2O_2$=2 mM/mL $H_2O_2$

The amount consumed by each PC catalyst in 5 minutes based on the percentages of consumption indicated in the above-mentioned Table 14 is as indicated below.

PEG-PC (15 mg)=2 mM/mL×0.147=294 μM/mL $H_2O_2$
Thus, 1 unit=15000-294≈50 μg/μM

CLPC (15 mg)=2 mM/mL×0.059=118 μM/mL $H_2O_2$
Thus, 1 unit=15000-118≈127 μg/μM

On the basis of the above results, the catalase activity of the amount of PEG-PC (50 μg) capable of converting 1 μmole of substrate ($H_2O_2$: MW 34) per 5 minutes was clearly determined to be 2.3 times the amount of CLPC (127 μg). This result was nearly identical to the result of observing bubbles generated by PEG-PC and CLPC indicated in Table 11.

According to the results of each of the above-mentioned examples, a correlation was obtained among the concentration of the iron component indicated in Table 1 (Fe: about 9 times), catalase activity indicated in Table 11 (2 times or more), PQQ-dehydrogenase and cytochrome c oxidase (asymmetric oxidation activity: about 2 to 4 times, 36 h to 48 h→13 h to 18 h). Namely, evaluation of bubbling following addition of 5% $H_2O_2$ in an 18 mm diameter centrifuge tube can be used as one method for easily confirming and measuring iron content and the amounts of PQQ-dehydrogenase/cytochrome c oxidase (asymmetric oxidation activity).

Example 21

(Efficacy of Continuous Reuse of CLPC-2 and PEG-PC)

The CLPC-2 used in Table 10 (20 mg: precipitate-derived PC obtained by centrifuging after precipitating with 30% ammonium sulfate) and PEG-PC (20 mg) were reacted under the reaction conditions of Example 14 after adding substrate Rac-2 (20,000 ppm, 30 μL) in 50 mM glycine-NaOH (pH 9.0, 0.4 mL)/DMSO (<1.0% (v/v)). Following completion of the reaction, hexane (4.0 mL) was added and recovered after reaching homogeneity, the hexane extract was quantified and measured for optical purity using an HPLC optical resolution column, and substrate Rac-2 (20,000 ppm, 30 μL) was added to each remaining PC catalyst solution to confirm the efficacy of repeated reuse thereof. The results of that continuous reuse are shown in Table 16.

TABLE 16

| Continuous Reuse | CLPC-2 | | PEG-PC | |
| --- | --- | --- | --- | --- |
| 1st Time | 24 h | >99% ee/~50% | 13 h | >99% ee/~50% |
| 2nd Time | 22 h | >99% ee/~50% | — | — |
| 3rd Time | 20 h | >99% ee/~50% | — | — |

Supplement: % ee;
optical purity, %: chemical yield

On the basis of the results of Table 16, PC chemically modified by glutaraldehyde does not undergo denaturation by extract solvent hexane, and was determined to be able to be reused up to three times without impairment of optical purity or yield. On the other hand, in the case of PC physically coated with a polymer compound (such as polyethylene glycol (PEG)), activity starting during the second use was lost as a result undergoing denaturation due to the solvent effects of hexane. However, as is indicated in FIG. 11(c), activity was not lost even during continuous addition of substrate (20,000 ppm, 30 μL) for three times each at 0 h, 12 h and 20 h after the start of the reaction, and optical resolution was able to occur at 30 h at a substrate concentration of about 1000 ppm. On the other hand, the reaction was unable to proceed after continuous addition of substrate for 3 times each.

On the basis of the above results, changing the manner in which the PC is immobilized, such as CLPC or HPC-PC, enables the protein complex to be used in various applications. Although both are equal in terms of thermostability, the chemically bound CLPC (continuous reuse type) is used in cases requiring solvent stability, while HPC-PC is used in the case of desiring to obtain optical resolving activity only once in consideration of edible applications or the environment.

With respect to whether the PC concentrate (centrifugal separation) obtained in the second step of FIG. 1 is subjected to chemical immobilization treatment or physical immobilization treatment, the object of the present invention is to provide a comprehensive method for using the PC, and various treatment methods and effects thereof have been clearly determined.

Example 22

(Selective Asymmetric Oxidative Synthesis of Both Enantiomers by PEG-PC)

Roughly 5 equivalents of concentrated PC precipitate was uniformly mixed in 50 mM glycine-NaOH buffer containing 0.5% to 1.0% (v/v) of polyethylene glycol (PEG: molecular weight 1000/4000=2/1) and allowed to stand undisturbed for 20 hours followed by centrifuging, vacuum freeze-drying (FD) the resulting precipitate and crushing. In this case, CLPC was confirmed in Table 17 to have PEG4000 prominently covering the PC surface in comparison with AGPC. The specific activities of CLPC and AGPC were 0.6 mU and 0.8 mU, respectively (refer to FIG. 19 for details), and the case of containing PEG having a molecular weight of 1000 exhibited more potent activity.

TABLE 17

Activities, Conditions and Mineral Compositions of Different Processed PC

| Forms (20 mg) | Product | Reactions (rac-1 or rac-2) | | | | Minerals[e] | |
| --- | --- | --- | --- | --- | --- | --- | --- |
| | | Solvent | Time (h) | Unit (mg • min) | Substrate (%) | $Ca^{2e}$ (%) | $Fe^{2e}$ (ppm) |
| $CLPC_b{}^a$ | S-1, S-2 ≥78% ee. ~50% $CY^b$ | Buffer[d] | 48 | Low | 0.02 | 0.45 ± 0.05 | 59 ± 2 |
| $CLPC_a{}^a$ | S-1, S-2 ≥99% ee. ~50% $CY^b$ | D.W.[c] | 16 | 0.6 ± 0.02 mU | ≥0.06 | 2.4 ± 0.2 | 220 ± 5 |
| PEG (4000)-PC | S-1, S-2 ≥99% ee. ~50% $CY^b$ | D.W. | 14 | 0.6 ± 0.02 mU | ≥0.06 | 2.6 ± 0.2 | 215 ± 5 |
| AGPC | R-1, R-2 ≥99% ee. ~50% $CY^b$ | D.W. | 9 | 0.8 ± 0.03 mU | ≥0.06 | 2.5 ± 0.2 | 213 ± 5 |

[a]$CLPC_a$ prepared without "$(NH_4)_7SO_4$" precipitation. $CLPC_b$ prepared with "$(NH_4)_2SO_4$" precipitation.
[b]Chemical yield (%).
[c]Distilled water.
[d]50 mM Glycine-NaOH (pH 9.0) or 50 mM Tris-HCl (pH 8.0).
[e]Mineral values were determined by ICP-AES: Mean ± SD (n = 4).

Based on a comparison with FIG. 3, as a result of further coating the surface of PC covered with 2.6% $Ca^{2+}$ with PEG, various PC activity, it was determined to have an effect of various PC activity, such as improvement of reaction rate and inversion of stereoselectivity. In the case of PC coated with PEG having a molecular weight of 4000, although a stereoselective oxidation reaction of the R-isomer of substrate Rac-2 occurred, in the case of PC coated with PEG having a molecular weight of 1000, it catalyzed a stereoselective oxidation reaction of the S-isomer. PEG coating the PC in a diluted aqueous solution was determined to act as an assistant that promotes permeability of the PC surface to substrate enabling it to penetrate to the active center.

Although detailed data is shown in Table 17 and FIG. 19, although the reaction was inverted from an R-isomer-selective oxidation reaction to an S-isomer-selective oxidation reaction with respect to Rac-1 and the like as a result of changing the molecular weight of PEG from 4000 to 1000, it must also not be overlooked that after oxidation of the S-isomer, the R-isomer was subsequently oxidized resulting in all isomers being oxidized to ketone. With respect to PEG-PC and CLPC using PEG having a molecular weight of 4000 (for which activity rate tends to decrease due to ammonium sulfate), it is also clear from this data that an interesting finding was obtained in which the S-isomer-selective oxidation reaction is hardly observed at all.

INDUSTRIAL APPLICABILITY

The protein complex having activity that catalyzes an asymmetric oxidation reaction of the present invention, and the production process thereof, are able to provide a novel asymmetric oxidation catalyst that enables optical isomers, such as optically active alcohol synthesized in the fields of pharmaceuticals, perfumes, foods and other fine chemical fields, to be easily produced inexpensively while being environmentally-friendly.

We claim:

1. A process for producing an iron-containing membrane protein complex from a plant, which has a reactivity with hydrogen peroxide even in the absence of NAD(H) and/or NADP(H), the process consisting of:
   a first step of oxidizing a plant-derived crude protein with oxygen, wherein the first step includes the following steps of (a1) to (a3):
   (a1) encapsulating the plant-derived protein in a gel,
   (a2) oxidizing the gel in air, and
   (a3) eluting the protein complex from the gel after the oxidation of the gel to obtain the oxidized product; and
   a second step of subjecting the oxidized product obtained in the first step to an immobilization process to form an iron-containing membrane protein complex, wherein the immobilization process is carried out by a polymer compound coating process, and the second step includes the following steps of (b1) to (b3):
   (b1) precipitating the membrane protein complex from an aqueous solution of the oxidized product obtained in the first step,
   (b2) dissolving the precipitated membrane protein complex in a buffer of pH 9 to 10 in co-presence with a polymer compound and glutaraldehyde to produce a polymer compound-coated membrane protein complex, and
   (b3) obtaining a dried polymer compound-coated membrane protein complex by subjecting the protein complex to dehydration, wherein the resultant protein complex is free of ammonium sulfate.

2. The process for producing an iron-containing membrane protein complex according to claim 1, wherein, in the step of (b2), the polymer compound in co-presence with 0.5 mM glycine-NaOH buffer (pH 9 to 10) is 0.5% to 1.0% (v/v) and the glutaraldehyde is 1.0% to 3.0%.

3. The process for producing an iron-containing membrane protein complex according to claim 1, wherein the polymer compound-coated membrane protein complex obtained in the second step is subjected to powderization treatment.

4. The process for producing an iron-containing membrane protein complex according to claim 1, wherein the polymer compound has a molecular weight of 4000 or more.

5. The process for producing an iron-containing membrane protein complex according to claim 4, wherein the polymer compound is polyethylene glycol.

6. The process for producing an iron-containing membrane protein complex according to claim 1, wherein the polymer compound is a mixture of polymer compounds having different molecular weights, and
   the mixture is composed of a polymer compound having a molecular weight of 4000 or more and a polymer compound having a molecular weight of 1000 or less, and contains one-third or less of the low molecular weight polymer compound.

7. The process for producing an iron-containing membrane protein complex according to claim 6, wherein the polymer compound is polyethylene glycol.

* * * * *